United States Patent
Wong

(10) Patent No.: US 9,296,611 B2
(45) Date of Patent: Mar. 29, 2016

(54) ZIRCONIUM PHOSPHATE PARTICLES HAVING IMPROVED ADSORPTION CAPACITY AND METHOD OF SYNTHESIZING THE SAME

(71) Applicant: Fresenius Medical Care Holdings, Inc., Waltham, MA (US)

(72) Inventor: Raymond June-Hin Wong, Norman, OK (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 120 days.

(21) Appl. No.: 14/247,261

(22) Filed: Apr. 8, 2014

(65) Prior Publication Data

US 2014/0248204 A1    Sep. 4, 2014

Related U.S. Application Data

(62) Division of application No. 14/083,468, filed on Nov. 19, 2013, now Pat. No. 8,733,559, which is a division of application No. 12/569,485, filed on Sep. 29, 2009, now Pat. No. 8,640,887.

(60) Provisional application No. 61/102,466, filed on Oct. 3, 2008.

(51) Int. Cl.
*B01J 20/06* (2006.01)
*B01J 20/28* (2006.01)
(Continued)

(52) U.S. Cl.
CPC ............ *C01B 25/372* (2013.01); *A61M 1/14* (2013.01); *B01D 15/362* (2013.01); *B01J 20/02* (2013.01); *B01J 20/28004* (2013.01); *B01J 20/28057* (2013.01); *B01J 20/28069* (2013.01);
(Continued)

(58) Field of Classification Search
CPC ............ B01J 20/0203; B01J 20/0211; B01J 20/0292; B01J 20/30; B01J 20/305; B01J 20/3071; B01J 20/3078; B01J 20/3085; B01J 39/085; B01J 39/12
See application file for complete search history.

(56) References Cited

U.S. PATENT DOCUMENTS 3,416,884 A    12/1968 Stynes
3,850,835 A    11/1974 Marantz et al.
(Continued)

FOREIGN PATENT DOCUMENTS

GB    1007871    10/1965
GB    1476641    6/1977
(Continued)

OTHER PUBLICATIONS

International Search Report and Written Opinion of the International Searching Authority issued in corresponding International Patent Application No. PCT/US2009/058808 dated Jun. 21, 2010 (22 pages).
(Continued)

*Primary Examiner* — Katherine Zalasky
(74) *Attorney, Agent, or Firm* — Kilyk & Bowersox, P.L.L.C.

(57) ABSTRACT

Zirconium phosphate particles are synthesized by providing a solution of zirconium oxychloride in an aqueous solvent, adding at least one low molecular weight, oxygen containing, monofunctional, organic additive to the solution, and combining this solution with heated phosphoric acid or a phosphoric acid salt to obtain zirconium phosphate particles by sol gel precipitation.

20 Claims, 1 Drawing Sheet

(51) Int. Cl.
*B01D 39/06* (2006.01)
*C01B 25/37* (2006.01)
*B01J 20/02* (2006.01)
*B01J 39/12* (2006.01)
*A61M 1/14* (2006.01)
*B01D 15/36* (2006.01)
*B01D 15/08* (2006.01)
*B01J 20/04* (2006.01)

(52) U.S. Cl.
CPC ...... *B01J 20/28083* (2013.01); *B01J 20/28085* (2013.01); *B01J 39/12* (2013.01); *C01B 25/37* (2013.01); *B01J 20/0211* (2013.01); *B01J 20/048* (2013.01); *Y10T 428/2982* (2015.01)

(56) References Cited

U.S. PATENT DOCUMENTS

| | | | |
|---|---|---|---|
| 4,381,289 | A | 4/1983 | Nowell et al. |
| 4,629,656 | A | 12/1986 | Alberti et al. |
| 4,826,663 | A | 5/1989 | Alberti et al. |
| 5,387,724 | A | 2/1995 | Johnstone et al. |
| 5,441,717 | A | 8/1995 | Ohsumi et al. |
| 6,332,985 | B1 | 12/2001 | Sherman et al. |
| 6,409,699 | B1 | 6/2002 | Ash |
| 6,579,460 | B1 | 6/2003 | Willis et al. |
| 6,627,164 | B1 | 9/2003 | Wong |
| 6,818,196 | B2 | 11/2004 | Wong |
| 6,878,283 | B2 | 4/2005 | Thompson |
| 6,936,175 | B2 | 8/2005 | Bortun et al. |
| 7,033,498 | B2 | 4/2006 | Wong |
| 7,101,519 | B2 | 9/2006 | Wong |
| 7,208,092 | B2 | 4/2007 | Micheli |
| 7,241,272 | B2 | 7/2007 | Karoor et al. |
| 7,252,767 | B2 | 8/2007 | Bortun et al. |
| 7,385,803 | B2 | 6/2008 | Alberti et al. |
| 7,566,432 | B2 | 7/2009 | Wong |
| 8,640,887 | B2 | 2/2014 | Wong |
| 2002/0112609 | A1 | 8/2002 | Wong |
| 2002/0123715 | A1 | 9/2002 | Sorenson et al. |
| 2003/0103888 | A1 | 6/2003 | Hai et al. |
| 2005/0274658 | A1 | 12/2005 | Rosenbaum et al. |
| 2006/0140840 | A1 | 6/2006 | Wong |
| 2006/0155030 | A1 | 7/2006 | Aupaix et al. |
| 2008/0051696 | A1 | 2/2008 | Curtin et al. |
| 2014/0069858 | A1 | 3/2014 | Wong |

FOREIGN PATENT DOCUMENTS

| | | |
|---|---|---|
| JP | 59069428 A | 4/1984 |
| JP | 62226807 A | 10/1987 |
| WO | WO 02/04086 A1 | 1/2002 |
| WO | 2004007359 A1 | 1/2004 |

OTHER PUBLICATIONS

Bellezza et al., "Zirconium phosphate nanoparticles from water-in-oil microemulsions," Colloid & Polymer Science, vol. 285, Aug. 3, 2006, pp. 19-25.

Tarafdar et al., "Synthesis of spherical mesostructured zirconium phosphate with acidic properties," Microporous and Mesoporous Materials, vol. 95, Jul. 14, 2006, pp. 360-365.

Cobe Renal Care, Inc., "Guide to Custom Dialysis," Product No. 306100-005, Revision E, Sep. 1993, pp. 1-52 (54 pages).

Cobe Renal Care, Inc., "Sorbent Dialysis Primer," Product No. 306100-006, Edition 4, Sep. 1993, pp. 1-46 (56 pages).

Jiménez-Jiménez et al., "Surfactant-Assisted Synthesis of a Mesoporous Form of Zircomium Phosphate with Acidic Properties," Advanced Materials, vol. 10, No. 10, 1998, pp. 812-815.

Pacheco et al., "Syntheses of Mesoporous Zirconia with Anionic Surfactants," J. Mater. Chem., vol. 8, No. 1, 1998, pp. 219-226.

Bogdanov et al., "Structure of Zirconium Phosphate Gels Produced by the Sol-Gel Method," Journal of Physics: Condensed Matter, vol. 9, 1997, pp. 4031-4039, (abstract only).

Ferragina et al., "Synthesis and Characterization of Sol-Gel Zirconium Phosphate with Template Surfactants by Different Methods," Journal of Thermal Analysis and Calorimetry, vol. 71, No. 3, 2003, pp. 1023-1033, (abstract only).

Sharygin et al., "Sol-Gel Technique for Production of Spherically Granulated Zirconium(IV) Phosphate," Russian Journal of Applied Chemistry, vol. 78, No. 2, 2005, pp. 229-234, (abstract.only).

Jignasa et al., "A Study on Equilibrium and Kinetics of Ion Exchange of Alkaline Earth Metals Using an Inorganic Cation Exchanger—Zirconium Titanium Phosphate," Journal of Chemical Science, vol. 118, No. 2, Mar. 2006, pp. 185-189.

Sun, Zhengfei, "Novel Sol-Gel Nanoporous Materials, Nanocomposites and Their Applications in Bioscience," Drexel University, Sep. 2005, pp. 27-62.

Ferragina et al., "Synthesis and Characterization of Sol-Gel Zirconium Phosphate with Template Surfactant", CNR, IMAI-ICMAT, via Salaria Km. 29.300, 00016, (year unknown), (abstract only).

ZIRCONIUM PHOSPHATE PARTICLES HAVING IMPROVED ADSORPTION CAPACITY AND METHOD OF SYNTHESIZING THE SAME

This application is a divisional of U.S. patent application Ser. No. 14/083,468, filed Nov. 19, 2013, which in turn is a divisional of U.S. patent application Ser. No. 12/569,485, filed Sep. 29, 2009 (now U.S. Pat. No. 8,640,887 B2), which in turn claims the benefit under 35 U.S.C. §119(e) of prior U.S. Provisional Patent Application No. 61/102,466, filed Oct. 3, 2008, which is incorporated in its entirety by reference herein.

FIELD OF INVENTION

The present invention relates to zirconium phosphate particles, and to methods of making zirconium phosphate particles, such as by sol gel synthesis, that have improved porosity, BET surface area, and/or ammonium ion adsorption properties.

BACKGROUND OF THE INVENTION

Zirconium phosphate (ZrP) particles are used as ion exchange materials and are particularly useful as a sorbent material for regenerative dialysis. Zirconium phosphate (ZrP) particles can be synthesized by a sol gel process using zirconium oxychloride (ZOC), also called zirconyl chloride, as a starting material. ZOC is a preferred starting material because it is abundant and commercially available at a low price.

Sol gel precipitation, as the term is used herein, refers generally to a process for forming a ceramic or catalyst in which colloidal particles (called sol) are formed by reacting hydrated metal ions (group III and IV) with a precipitating agent, followed by the polymerization of the colloidal particles to form gel particles. See, for example, Bogdanov S G et al., "Structure of zirconium phosphate gels produced by the sol-gel method," J. PHYS.: CONDENS. MATTER, Vol. 9, 4031-4039 (1997), incorporated herein by reference. Sol gel precipitation is a particularly advantageous method of obtaining zirconium phosphate from zirconium oxychloride since it is a direct, single-step conversion process that can be carried out at room temperature. Hence, it offers great advantages in efficiency and manufacturing costs in comparison with other processes. Moreover, zirconium phosphate particles obtained by sol gel precipitation generally have a high porosity and a high BET surface area, which enhances their adsorption capacity for ammonia. Further, the use of the sol gel precipitation method allows for control over particle size and morphology of the product, as well as control over impurity levels. These characteristics for zirconium phosphate particles are important with respect to ammonia adsorption and cartridge design for dialysis applications.

Despite all of these advantages, the sol gel precipitation is not easy to accomplish on a manufacturing scale. The difficulties are mainly caused by the nature of the raw material (e.g., ZOC), the rapid rate of the reaction, which is difficult to control, and the lack of appropriate process control methods (flow rate, agitation rate, concentration, etc.). These difficulties can be described as follows.

Sol gel zirconium phosphate, when precipitated directly from zirconium oxychloride solution using phosphoric acid as a precipitating agent, is in the form of soft gel particles having a wide range of particle sizes. One reason why this happens is that zirconium ions in a solution of zirconium oxychloride are highly hydrated monomers, that is, they are surrounded by a large number of coordinated water molecules. During the formation of zirconium phosphate, the soft gel particles tend to agglomerate when the product slurry gets thicker during the reaction process, or when the particles are packed during the filtration and drying process. As a result of this agglomeration, large aggregates are present in the end product after drying so that milling or grinding is required to obtain a free-flowing powder, with the further disadvantage that milling produces a lot of excessively fine particles. Agglomeration also increases the particle size to an extent that is undesirable for column or separation applications.

A wide range of particle sizes in the finished product is a common result of the conventional sol gel precipitation process for the additional reason that the particle size depends on the concentration of the reactants, which gradually decreases as precipitation continues, causing the formation of smaller particles. Thus, it is difficult to control particle size using a single reactant addition technique. Large particles and excessively fine particles are both undesirable for dialysis application because large particles can cause ammonia leakage and smaller adsorption capacity, while fine particles can increase flow resistance and pressure drop in a sorbent cartridge.

Further, the agglomeration of sol gel zirconium phosphate during the precipitation process interferes with agitation and mixing of the reactants as the slurry concentration increases, resulting in the formation of an excessive number of fine particles.

The particle size of sol gel zirconium phosphate can be increased by increasing the amount and concentration of phosphoric acid (for example, by providing a ratio of $ZrO_2$:$PO_4$ of 1:3) but the increase in phosphoric acid also enhances the gelation effect as excess lattice Er in ZrP combines with $H_2O$ molecules.

Recent advances in sol gel precipitation provide a method of synthesizing zirconium phosphate particles that avoids the creation of soft gel particles and/or that avoids agglomeration of zirconium phosphate gel particles. U.S. Patent Application Publication No. 2006/0140840, which is incorporated in its entirety by reference herein, describes a method for synthesizing zirconium phosphate particles that utilizes organic chemical additives to suppress gelation and agglomeration in order to control particle size of the product. The additive is added to a zirconium oxychloride solution and can form a complex with zirconium ions in the solution and thereby reduce hydration of the zirconium ions. The solution can then be combined with phosphoric acid or a phosphoric acid salt to obtain zirconium phosphate particles by sol gel precipitation. The method can synthesize zirconium phosphate particles having a controlled particle size or particle size distribution. Zirconium phosphate particles synthesized by this method can have, for example, a particle size distribution of less than 20% in the range of >60-120 microns, more than 80% in the range of 30-60 microns, and less than 10% in the range of less than 30 microns. The particles can also have an ammonia capacity in dialysate solution of about 15-20 mg $NH_4^+$—N/g ZrP, when exposed to an $NH_4^+$—N/g concentration of 100 mg/dL.

Despite the controlled particle size and tight particle size distribution, the zirconium phosphate particles may reflect a larger particle size than desired, and lower than expected ammonium ion adsorption capacity. Residual organic additives may be tightly bound to the ZrP lattice and as a result, the porosity and BET surface area of the particles may be less than expected.

Accordingly, there is a need for an improved method of synthesizing zirconium phosphate particles that overcomes one or more of the above-mentioned disadvantages.

There is a need for a sol gel preparation method that removes any residual organic additives from the sol gel ZrP product, thus improving porosity, BET surface area, and $NH_4^+$ adsorption capacity.

There is a particular need for ZrP particles smaller than about 5 microns that can have enhanced $NH_4^+$ adsorption capacity sol gel ZrP particles for sorbent applications including portable sorbent dialysis systems.

SUMMARY OF THE INVENTION

A feature of the present invention is to provide zirconium phosphate particles that avoid one or more of the above-mentioned disadvantages.

A feature of the present invention is to provide zirconium phosphate particles having a desirable hardness, particle size, particle size range, shape, packing density, porosity, BET surface area for adsorption, and/or adsorption capacity.

Another feature of the present invention is to provide zirconium phosphate particles having improved porosity, BET surface area, and/or ammonium ion adsorption capacity.

Another feature of the present invention is to provide zirconium phosphate particles having an average particle size of less than 5 microns.

A further feature of the present invention is to provide zirconium phosphate particles prepared by sol gel precipitation having no (or essentially no) residual organic molecules bound to the particle.

A feature of the present invention is to provide a method of synthesizing zirconium phosphate particles by a sol gel technique that avoids one or more of the above-mentioned disadvantages.

Another feature of the present invention is to provide a method of synthesizing zirconium phosphate particles by a sol gel technique that avoids the creation of soft gel particles and/or that avoids agglomeration of zirconium phosphate gel particles, and that does not result in residual organic molecules bound to the particles to reduce porosity, BET surface area, and/or ammonia adsorption capacity.

Additional advantages of the present invention will be set forth in part in the description that follows, and in part will be apparent from the description, or may be learned by practice of the present invention. The goals and advantages of the present invention will be realized and attained by means of the elements particularly pointed out in the appended claims.

To achieve the above noted goals and in accordance with the purposes of the present invention, as embodied and broadly described herein, the present invention provides a composition comprising a water-soluble zirconium-containing polymer complex in an aqueous solution, wherein the polymer complex is formed by combining, in an aqueous solvent, zirconium oxychloride with at least one low molecular weight, oxygen containing, monofunctional, organic additive. The additive can form a complex with zirconium ions in the solution.

The present invention also provides zirconium phosphate particles synthesized by a sol gel precipitation that do not include tightly bound residual organic compounds.

The present invention further provides zirconium phosphate particles having one or more of the following characteristics: an average particle size of less than 5 microns, an ammonia capacity in dialysate solution of at least 15 mg $NH_4$—N/g ZrP when exposed to 100 mg/dL of $NH_4$—N, and/or a BET surface area of at least about 10 $m^2$/g ZrP.

The present invention further provides a portable dialysis system comprising a container that contains such zirconium phosphate particles.

The present invention further provides zirconium phosphate particles comprising one or more of the following characteristics: an average particle size of from about 40-50 microns, an ammonia capacity in dialysate solution of at least 15 mg $NH_4$—N/g ZrP when exposed to 100 mg/dL of NH—N, and/or a BET surface area of at least about 10 $m^2$/g ZrP.

The present invention further provides a dialysis cartridge comprising a cartridge that contains such zirconium phosphate particles.

The present invention further provides zirconium phosphate particles comprising one or more of the following characteristics: an average particle size of from about 45-90 microns, an ammonia capacity in dialysate solution of at least 15 mg $NH_4$—N/g ZrP when exposed to 20 mg/dL of $NH_4$—N, and/or a BET surface area of at least about 2 $m^2$/g ZrP.

The present invention further provides a dialysis cartridge comprising a cartridge that contains such zirconium phosphate particles.

The present invention further provides zirconium phosphate particles comprising one or more of the following characteristics: a pore volume of at least 0.0071 mL/g, a monolayer volume of at least 0.5 mL/g (STP), and/or a 20-80 nm pore size content of at least 30%. These porosity and pore size properties can apply to any particle size, including any particle size range indicated herein. Also, for example, these particles can have a BET surface area of at least about 2 $m^2$/g ZrP, or at least about 5 $m^2$/g ZrP, or at least about 10 $m^2$/g ZrP.

The present invention further provides a dialysis cartridge comprising a cartridge that contains such zirconium phosphate particles.

The present invention also provides a method of making zirconium phosphate particles by combining zirconium oxychloride and at least one low molecular weight, oxygen containing, monofunctional, organic additive, in an aqueous solvent to form a solution. The low molecular weight, oxygen containing, monofunctional, organic additive(s) can form a complex with zirconium ions in the solution and thereby reduce hydration of the zirconium ions. The organic additive can prevent agglomeration of the zirconium phosphate particles in sol gel precipitation, and thereby increase the porosity and/or BET surface area of the particles. Zirconium phosphate particles having increased porosity and/or BET surface area can have improved ammonia adsorption capacity.

The low molecular weight, oxygen containing, monofunctional, organic additive(s) either does not bind or tightly bind to the zirconium phosphate particles. Accordingly, the method further includes combining the solution with phosphoric acid or a phosphoric acid salt, and then removing the low molecular weight, oxygen containing, monofunctional, organic additive to obtain zirconium phosphate particles free of (or essentially free of) residual additive by sol gel precipitation. The low molecular weight, oxygen containing, monofunctional, organic additive can be removed, for example, by evaporating the additive to obtain zirconium phosphate particles that are free of (or essentially free of) residual organic additive. The phosphoric acid or phosphoric acid salt can be at boiling temperature, for example, a temperature of from about 90° C.-100° C., or about 96° C. The low molecular weight, oxygen containing, monofunctional, organic additive can also be removed, such as by washing the zirconium phosphate particles, for example, with water, to remove residual organic additive. Other removal techniques can be used.

The low molecular weight, oxygen containing, monofunctional, organic additive can be removed by any technique, such as by heat and/or washing, and the like. For purposes of the present invention, the "removal" of the additives can include total removal of the additive and/or substantial removal of the additive, such as preferably below 1 wt % (e.g., 0 wt % to 0.9 wt %, 0.0001 wt % to 0.7 wt %, 0.001 wt % to 0.5 wt %, 0.01 wt % to 0.25 wt %) of the additive remaining, based on the total weight of the additive present prior to the removal. Subjecting the zirconium phosphate particles to heat, such as the boiling temperature of the phosphoric acid, can evaporate a low molecular weight, oxygen containing, monofunctional, organic additive and remove the residual additive from the zirconium phosphate particles, thus optionally increasing porosity and/or BET surface area. The heat step can have a hardening effect on the particles and/or improve the crystal structure of the particles. Hardened zirconium phosphate particles can be dried without suffering from particle collapse and/or agglomeration. The method can optionally further include subjecting an aqueous slurry containing the zirconium phosphate particles to additional heat treatment, for example, for about 1-2 hrs, for instance, at a temperature of, for example, from about 90° C.-100° C.

The present invention further provides a method of synthesizing zirconium phosphate particles having a controlled particle size or particle size distribution. The method includes combining a solution of zirconium oxychloride and low molecular weight, oxygen containing, monofunctional, organic additive with a solution of phosphoric acid or a phosphoric acid salt and evaporating the low molecular weight, oxygen containing, monofunctional, organic additive to obtain zirconium phosphate particles by sol gel precipitation. For instance, the method can include providing a reaction vessel having an agitator and adding a solution of zirconium oxychloride and a solution of phosphoric acid or a phosphoric acid salt, such as simultaneously (or other orders of addition) to the reaction vessel so that zirconium ions react with the phosphoric acid or a phosphoric acid salt to obtain zirconium phosphate particles by sol gel precipitation. The particle size and/or particle size distribution of the zirconium phosphate particles obtained can be controlled by controlling at least one or more of the following parameters: the rate at which the solution of zirconium oxychloride is added to the reaction vessel, the rate at which the solution of phosphoric acid or phosphoric acid salt is added to the reaction vessel, the pH of the solution of phosphoric acid or phosphoric acid salt, the concentration of each component, i.e., zirconium oxychloride, low molecular weight, oxygen containing, monofunctional, organic additive, and/or phosphoric acid or a phosphoric acid salt in the reaction vessel, the addition of hydrochloric acid (HCl) to the reaction, the speed of the agitator, or combinations thereof.

The present invention further provides a method of synthesizing zirconium phosphate particles by combining zirconium oxychloride and at least one low molecular weight, oxygen containing, monofunctional, organic additive in an aqueous solvent, to form a solution wherein the low molecular weight, oxygen containing, monofunctional, organic additive(s) can form a complex with zirconium ions in the solution, which can reduce hydration of the zirconium ions, combining the solution with phosphoric acid or a phosphoric acid salt, and evaporating the at least one low molecular weight, oxygen containing, monofunctional, organic additive to obtain zirconium phosphate particles by sol gel precipitation. The method can further include subjecting an aqueous slurry containing the zirconium phosphate particles to a heat treatment.

It is to be understood that both the foregoing general description and the following detailed description are exemplary only and are not restrictive of the present invention, as claimed.

The accompanying drawings, which are incorporated in and constitute a part of this application, illustrate some of the embodiments of the present invention and together with the description, serve to explain the principles of the present invention.

DETAILED DESCRIPTION OF THE PRESENT INVENTION

Figure 1:
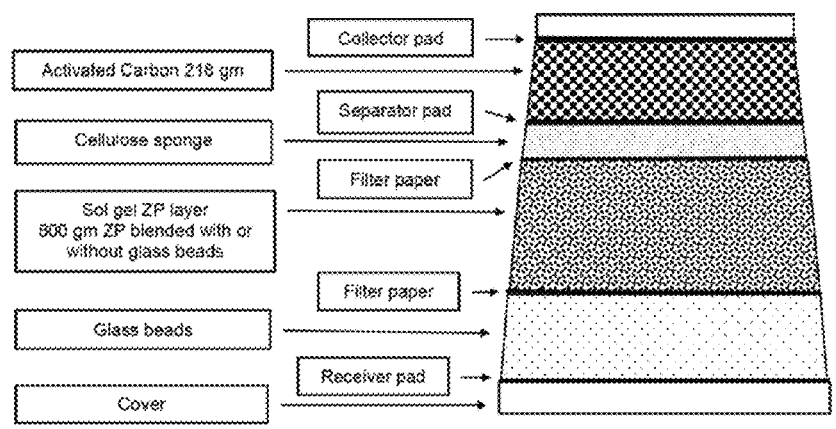
FIG. 1 is a cross-section of a sorbent cartridge used for a product quality-cartridge performance test based on $NH_4^+$—N adsorption capacity of the cartridge.

The present invention relates in part to zirconium phosphate particles having improved porosity, BET surface area, and/or ammonium ion adsorption capacity. The zirconium phosphate (ZrP) particles can have, for example, one or more of the following characteristics: an average particle size of less than 5 microns, for example, from about 2 to 4.9 microns or from about 1 to about 3 microns or from about 0.5 to about 4 microns, an ammonia capacity in dialysate solution of at least 15 mg $NH_4$—N/g ZrP when exposed to 100 mg/dL of $NH_4$—N, and/or a BET surface area of at least about 10 $m^2$/g ZrP (e.g., 10 $m^2$/g ZrP to 100 $m^2$/g ZrP or more, 15 $m^2$/g ZrP to 100 $m^2$/g ZrP, or 20 $m^2$/g ZrP to 100 $m^2$/g ZrP). Preferably, the ZrP particles can have an ammonia capacity in dialysate solution of at least 20 mg $NH_4$—N/g ZrP, and more preferably, at least 25 mg $NH_4$—N/g ZrP, or at least 30 mg $NH_4$—N/g ZrP (such as 21 to 35 mg $NH_4$—N/g ZrP), when exposed to 100 mg/dL of $NH_4$—N. The ZrP particles can have an ammonia capacity in dialysate solution of, for example, from about 23-26 mg $NH_4$—N/g ZrP, when exposed to 100 mg/dL of $NH_4$—N, and/or an ammonia capacity of, for example, from about 7-9 mg $NH_4$—N/g ZrP, when exposed to 10 mg/dL of $NH_4$—N.

For purposes of this invention, a "dialysate solution" means a solution that can be used in hemodialysis or peritoneal dialysis, and, for example, having a sodium chloride concentration of about 105 mEq, and a sodium bicarbonate concentration of about 35 mEq. The sodium concentration of the dialysate solution can affect the ZrP ammonia capacity, and the ZrP particles can have an ammonia capacity in pure water that is greater than the ammonia capacity in dialysate solution. The ZrP particles can have an ammonia capacity in pure water of, for example, greater than 35 mg $NH_4$—N/g ZrP, when exposed to 100 mg/dL of $NH_4$—N, greater than 30 mg $NH_4$—N/g ZrP when exposed to 20 mg/dL of $NH_4$—N, for example, from about 30-38 mg $NH_4$—N/g ZrP, and greater than 20 mg $NH_4$—N/g ZrP when exposed to 10 mg/dl of $NH_4$—N, for example, from about 20-28 mg $NH_4$—N/g ZrP.

The zirconium phosphate particles of the present invention can be synthesized, for example, by combining zirconium oxychloride (ZOC) with at least one low molecular weight, oxygen containing, monofunctional, organic additive in an aqueous solvent to form a solution (organic additive-ZOC solution), combining the solution with phosphoric acid, and evaporating, and/or washing away, the low molecular weight, oxygen containing, monofunctional, organic additive to obtain zirconium phosphate particles by sol gel precipitation that are free (or essentially free) of residual organic additive.

The low molecular weight, oxygen containing, monofunctional, organic additive can be evaporated, for example, by vacuum, and/or heat. The organic additive-ZOC solution can be combined with heated phosphoric acid at a temperature high enough to evaporate the organic additive, for example, up to the boiling temperature of phosphoric acid, or phosphoric acid at a temperature of, for example, from about 90° C.-100° C.

The present invention also relates in part to zirconium phosphate particles having one or more of the following characteristics: an average particle size of from about 25-65 microns, for example, about 40-50 microns, an ammonia capacity in dialysate solution of at least 15 mg $NH_4$—N/g ZrP when exposed to 100 mg/dL of $NH_4$—N, and a BET surface area of at least about 10 $m^2$/g ZrP (e.g., 10 $m^2$/g ZrP to 100 $m^2$/g ZrP or more, 15 $m^2$/g ZrP to 100 $m^2$/g ZrP, or 20 $m^2$/g ZrP to 100 $m^2$/g ZrP). Preferably, the ZrP particles can have an ammonia capacity in dialysate solution of at least 20 mg $NH_4$—N/g ZrP, more preferably at least 25 mg $NH_4$—N/g ZrP, or at least 30 mg $NH_4$—N/g ZrP (e.g., 25 to 35 mg $NH_4$—N/g ZrP), when exposed to 100 mg/dL of $NH_4$—N. The ZrP particles can have an ammonia capacity in dialysate solution of, for example, from about 21-23 mg $NH_4$—N/g ZrP, when exposed to 100 mg/dL of $NH_4$—N, and/or an ammonia capacity of, for example, from about 6-8 mg $NH_4$—N/g ZrP, when exposed to 10 mg/dL of $NH_4$—N.

The present invention also relates in part to zirconium phosphate particles having one or more of the following characteristics: an average particle size of from about 45-840 microns, for example, about 45-90 microns, an ammonia capacity in dialysate solution of at least 15 mg $NH_4$—N/g ZrP when exposed to 20 mg/dL of $NH_4$—N, and a BET surface area of at least about 2 $m^2$/g ZrP (e.g., 2 $m^2$/g ZrP to 100 $m^2$/g ZrP or more, or 5 $m^2$/g ZrP to 100 $m^2$/g ZrP, or 10 $m^2$/g ZrP to 100 $m^2$/g ZrP, or 15 $m^2$/g ZrP to 75 $m^2$/g ZrP, or 20 $m^2$/g ZrP to 50 $m^2$/g ZrP). Preferably, the ZrP particles can have an ammonia capacity in dialysate solution of at least 15 mg $NH_4$—N/g ZrP, and more preferably, at least 20 mg $NH_4$—N/g ZrP, or at least 25 mg $NH_4$—N/g ZrP (such as 20 to 35 mg $NH_4$—N/g ZrP, or 21 to 30 mg $NH_4$—N/g ZrP, or 22 to 25 mg $NH_4$—N/g ZrP), when exposed to 20 mg/dL of $NH_4$—N. The ZrP particles also can have an ammonia capacity in dialysate solution of at least 20 mg $NH_4$—N/g ZrP, or at least 25 mg $NH_4$—N/g ZrP, or at least 30 mg $NH_4$—N/g ZrP (such as 20 to 35 mg $NH_4$—N/g ZrP, or 22 to 30 mg $NH_4$—N/g ZrP, or 24 to 28 mg $NH_4$—N/g ZrP), when exposed to 30 mg/dL of $NH_4$—N. The ZrP particles also can have an ammonia capacity in pure water of at least 25 mg $NH_4$—N/g ZrP, or at least 30 mg $NH_4$—N/g ZrP, or at least 40 mg $NH_4$—N/g ZrP (such as 25 to 55 mg $NH_4$—N/g ZrP, or 30 to 50 mg $NH_4$—N/g ZrP, or 35 to 45 mg $NH_4$—N/g ZrP), when exposed to 20 mg/dL of $NH_4$—N. The ZrP particles also can have an ammonia capacity in pure water of at least 30 mg $NH_4$—N/g ZrP, or at least 35 mg $NH_4$—N/g ZrP, or at least 45 mg $NH_4$—N/g ZrP (such as 30 to 65 mg $NH_4$—N/g ZrP, or 35 to 60 mg $NH_4$—N/g ZrP, or 40 to 55 mg $NH_4$—N/g ZrP), when exposed to 30 mg/dL of $NH_4$—N.

The present invention also relates in part to zirconium phosphate particles having one or more of the following characteristics: a pore volume of at least 0.0071 mL/g (e.g., 0.0071 to 0.15 mL/g, or 0.0075 to 0.125 mL/g, or 0.01 to 0.1 mL/g, or 0.02 to 0.09 mL/g), a (Langmuir) monolayer volume of at least 0.5 mL/g (STP) (e.g., 0.5 to 10 mL/g (STP), or 1 to 8 mL/g (STP), or 2.5 to 6.5 mL/g (STP), or 3 to 5 mL/g (STP)), and/or a 20-80 nm pore size content of at least 30% (e.g., 30% to 60%, or 32% to 55%, or 38% to 52%, or 42% to 50%). As indicated, these porosity and pore size properties can apply to any particle size, including any particle size range indicated herein. The pore size content refers to the percentage of all particle surface pores that have a pore size in the 20-80 nm range.

The particles with these porosities and pore sizes also can have, for example, one or more of the BET surface area, the ammonia capacity in dialysate solution, and/or the ammonia capacity in pure water, for any ZrP particles such as indicated herein, including, for example, but not limited to, the ZrP particles having an average particle size of from about 45-90 microns. The particle size range values indicated herein as average particle sizes can in addition or alternatively refer to a particle size fraction. For example, a particle size given as 45-90 microns herein, also can refer to the fraction of a particulate sample of which the particles have absolute particle sizes within that range.

The zirconium phosphate particles of the present invention can be synthesized, for example, by combining zirconium oxychloride (ZOC) with at least one low molecular weight, oxygen containing, monofunctional, organic additive in an aqueous solvent to form a solution, adding acid, like concentrated hydrochloric acid (HCl) to the solution, then combining the solution with an acid, like phosphoric acid, and evaporating or otherwise removing essentially all of the low molecular weight, oxygen containing, monofunctional, organic additive to obtain zirconium phosphate particles by sol gel precipitation. The addition of an acid, like HCl, can affect the average zirconium phosphate particle size. The size of the zirconium phosphate particles can be varied to obtain particles of a desired size, for example, an average particle size of from about 10-100 microns, about 10-25 microns, about 20-40 microns, about 25-65 microns, or about 40-50 microns. Without being bound to any theory, an acid, like HCl, may affect particle size by removing functional $OH^-$ groups from the zirconium phosphate polymerization reaction, thus allowing the polymerization reaction to continue and growing the particle size.

The present invention further relates to a composition formed as an intermediate in the method of the present invention by combining a zirconium oxychloride solution with a low molecular weight, oxygen containing, monofunctional, organic additive to form a water-soluble polymer complex, as described above. The amount of low molecular weight, oxygen containing, monofunctional, organic additive can depend on the particular additive and can be readily determined by performance studies. The amount of low molecular weight, oxygen containing, monofunctional, organic additive can be a minimum amount that is effective to improve the particle size of the product. Examples of suitable amounts are provided below.

A dialysis cartridge comprising a cartridge that contains the zirconium phosphate particles described herein is also a part of the present invention. The dialysis cartridge can be a cartridge that contains the zirconium phosphate particles, wherein the zirconium phosphate particles can be present as at least one layer and the dialysis cartridge further can comprise at least one other layer(s) of sorbent material. A portable dialysis system comprising a container that contains the zirconium phosphate particles described herein is also a part of the present invention. The container can contain, for example, zirconium phosphate particles as described above, for instance, having an average particle size of less than 5 microns, for example, about 2-5 microns, an ammonia capacity in dialysate solution of at least 25 mg $NH_4$—N/g ZrP when exposed to 100 mg/dL of $NH_4$—N, and a BET surface area of at least about 10 $m^2$/g ZrP.

The ZrP of the present invention can be used in any application where ZrP is used and can be used as the ZrP layer or as an additional ZrP layer in sorbent cartridges described in U.S. Patent Application Publication No. 2002-0112609 and U.S. Pat. No. 6,878,283 B2, and in Sorb's REDY cartridge (e.g., see "Sorbent Dialysis Primer," COBE Renal Care, Inc. Sep. 4, 1993 edition, and "Rx Guide to Custom Dialysis," COBE Renal Care, Inc. Revision E, September, 1993), all incorporated in their entirety by reference herein. All embodiments using ZrP in these published applications are embodiments of the present application wherein the ZrP of the present invention is used. For example purposes only, various filter media sections within a tubular housing or cartridge can be used with the ZrP particles of the present invention. The housing or cartridge can include a sorbent material like a granular activated carbon section, an immobilized enzyme section, a powdered alumina ($Al_2O_3$) section, a zirconium phosphate, and/or a section that includes a mixture of hydrous zirconium oxide of the acetate form and sodium zirconium carbonate, or sodium zirconium carbonate alone. The dialysis cartridge can be a cartridge that contains as one or more layers or zones the zirconium phosphate particles, wherein the dialysis cartridge has a plurality of filter media sections (or layers) including an arrangement, starting from a first end and ending at a second end, an activated carbon section, an immobilized enzyme section, a powdered alumina section, a zirconium phosphate section, and a sodium zirconium carbonate or a mixture of hydrous zirconium oxide of the acetate form and sodium zirconium carbonate section. For hemodialysis, a filter medium adapted to remove chlorine from tap water is preferred unless highly purified water is used as a base for the dialysate. The medium can be activated carbon. Activated carbon can be used as a filter medium to bind heavy metals, oxidants, and chloramines. An immobilized enzyme such as urease can be used in a filter medium to convert urea to ammonium carbonate by enzymatic conversion. Urease can be immobilized by adsorption, covalent bonding, intermolecular cross-linking, entrapment within cross-linked polymers, microencapsulation, and containment within a semipermeable membrane device. Alumina ($Al_2O_3$), activated carbon, anion exchange resins, and diatomaceous earth can be used as adsorbents. Urease can be used to covalently bond water-insoluble polymers to form enzyme-polymer conjugates via activation procedures or reactive polymers. Multifunctional reagents, for example, glutaraldehyde and hexamethylene diamine can be used to affect intermolecular cross-linking of urease. Urease can be entrapped within a cross-linked polymer, such as, for example, polyacrylamide gel. Urease can be microencapsulated using, for example, nylon, cellulose nitrate, ethyl cellulose, or polyamide. Urease can be contained within some permeable membrane device, such as, for example, AMICOM ultra-filtration cells, available from Fisher Scientific, Pittsburgh, Pa., or DOW hollow fiber beaker device, from The Dow Chemical Co., Midland, Mich. The use of activated carbon to remove chlorine, if used, can precede the immobilized enzyme medium because chlorine can deactivate the enzyme. Cation exchange materials can be used to bind ammonium, calcium, magnesium, potassium, and other cations as well as toxic trace metals in tap water. Another function of these filter media can be to convert carbonate from urea hydrolysis to bicarbonate. Such cation exchange materials can include zirconium phosphate, titanium phosphate, or zeolite. Anion exchange filter media bind phosphate, fluoride, and other heavy metals. By-products of the anion exchange filter media can include acetate and bicarbonate, which also corrects for metabolic acidosis of a patient's blood. Such filter media can include hydrous zirconium oxide of the acetate form, hydrous silica, stannic oxide, titanium oxide, antimonic acid, hydrous tungsten oxide, or sodium zirconium carbonate.

The present invention relates in part to a method of synthesizing zirconium phosphate particles by a sol gel technique using a solution of zirconium oxychloride in which the hydration of zirconium ions in the solution has been reduced. This can be accomplished, for example, by the use of an additive or additives in the zirconium oxychloride solution to change the zirconium ions in the solution from a highly hydrated monomeric form to a soluble polymeric zirconium complex with a high number of polymer units and a reduced water of hydration.

The present invention relates to a method of making zirconium phosphate particles comprising: (a) combining at least one low molecular weight, oxygen containing, monofunctional, organic additive with zirconium oxychloride in an aqueous solvent to form a solution wherein the low molecular weight, oxygen containing, monofunctional, organic additive forms a complex with zirconium ions in the solution, and (b) combining the solution obtained in (a) with phosphoric acid and evaporating the low molecular weight, oxygen containing, monofunctional, organic additive to obtain zirconium phosphate particles by sol gel precipitation. As typical, non-limiting amounts, the at least one low molecular weight, oxygen containing, monofunctional, organic additive can be present in an amount of from about 20 wt % to 70 wt % by weight of the zirconium oxychloride (e.g., 25 wt % to 60 wt %, 30 wt % to 50 wt % additive) and/or the molar ratio of zirconium oxychloride to phosphoric acid can be from 1:2.8 to 1:3.2. Other amounts and molar ratios below and above these ranges can be used. The aqueous solvent can be deionized water or reverse osmosis (RO) water. The zirconium oxychloride can be dissolved (or otherwise mixed) in the aqueous solvent and then the low molecular weight, oxygen containing, monofunctional, organic additive can be added to form the solution of step (a). The zirconium oxychloride can be dissolved (or otherwise mixed) in the aqueous solvent and then the low molecular weight, oxygen containing, monofunctional, organic additive can be added to form the solution of step (a). The zirconium oxychloride can be present in the aqueous solvent up to a saturation concentration or other concentration levels. The low molecular weight, oxygen containing, monofunctional, organic additive can be dissolved (or otherwise mixed) in the aqueous solvent and then the zirconium oxychloride can be added to form the solution of step (a). The low molecular weight, oxygen containing, monofunctional, organic additive can be present in the solution of step (a) in a molar amount sufficient so that all or substantially all of the zirconium ions in the solution are converted to a complex. The low molecular weight, oxygen containing, monofunctional, organic additive can form a soluble polymer complex with zirconium ions.

To explain how a low molecular weight, oxygen containing, monofunctional, organic additive can affect the characteristics of zirconium phosphate formed in a sol gel process, it helps to understand the nature of the zirconium ions in a zirconium oxychloride solution in the absence of an additive. Zirconium ions in a zirconium oxychloride solution by itself are highly hydrated zirconium species with 4-8 molecules of $H_2O$ coordinated with each zirconium (Zr) atom. The hydrated ions can form polymeric units ranging from a monomer, $ZrOOH^+$, to a tetramer, $Zr_4(OH)_8^{+8}$, depending on the concentration of the solution. As phosphoric acid is mixed with a zirconium oxychloride solution at room temperature, a sol gel zirconium phosphate precipitate is formed at a very rapid rate, trapping a large number of coordinated water molecules (or hydronium ions since the lattice $H^+$ can combine with $H_2O$ molecules to form $H_3O^+$) within the gel particle to form a soft gel. As discussed above, these soft gel particles can have a tendency to agglomerate as the slurry gets denser and when the material is packed on a filter during filtration or on trays during drying.

Using at least one low molecular weight, oxygen containing, monofunctional, organic additive preferably forms new zirconium polymeric species in solution having a reduced number of coordinated water molecules and a high polymer unit so that when these zirconium polymeric species react with phosphoric acid, the problems described above that arise from excessive hydration do not occur. In particular, the reaction of zirconium ions with phosphate is slowed, which allows for the concentration of reactants to be more easily controlled, thereby allowing for the particle size and/or particle size distribution of the particles formed by precipitation to be controlled. Because of the reduced water content, the particles formed by precipitation are harder and/or less prone to agglomeration and/or have a more refined molecular structure. If the low molecular weight, oxygen containing, monofunctional, organic additive that is used also has properties of an emulsifying agent, it is possible to improve the shape of the particles formed by precipitation from irregular to roughly or nearly spherical to spherical. Doing so may reduce or eliminate the agglomeration problem during drying, allowing for the formation of a free-flowing powder. Even if the particle size is kept small, the flow performance for column application can be improved. Except as otherwise provided herein, the synthesis of zirconium phosphate particles by the sol-gel process can be carried out according to known sol-gel techniques. For example, the aqueous solution used to initially dissolve the zirconium oxychloride can be water purified to remove ionic impurities such as trace metals by reverse osmosis (RO water) or by any other method that provides a low enough level of contaminants to be acceptable for the intended end use of the zirconium phosphate particle or can be deionized water. For carrying out the sol-gel precipitation, either phosphoric acid or a salt solution of phosphate can be used. At a high pH (e.g., about 4 pH or above), the use of a phosphate salt results in a product with a reduced ammonium capacity. Reference to phosphoric acid can include orthophosphoric acid, pyrophosphoric acid, tripolyphosphoric acid, tetrapolyphosphoric acid, trimetaphosphoric acid, and/or phosphoric anhydride, or combinations thereof. The phosphoric acid can have a molarity of 1 mole/L or higher, for instance, 1.5 moles/L to 3 moles/L, or 2.6 to 2.8 moles/L.

The low molecular weight, oxygen containing, monofunctional, organic additive used in the present invention can be capable of displacing water molecules that are coordinated to zirconium ions in an aqueous solution of zirconium oxychloride and that can preferably bridge zirconium ions to form a water soluble polymer species. More than one type of additive can be used, e.g., mixtures. The additive can be selected so that it can be displaced from the zirconium ions during the reaction with phosphoric acid or phosphate that forms zirconium phosphate. The additive can lead to the formation of polymer species that are preferably soluble in water. Accordingly, additives that are preferred in the present invention include alcohols and/or carboxylic acids comprising a single functional group (i.e., monofunctional), that are soluble in water. For purposes of this invention, a monofunctional compound can be an organic compound whose chemical structure possesses a single reactive site (e.g., a single reactive —OH group).

Examples of low molecular weight, oxygen containing, monofunctional, organic additives that can be used in the present invention include alcohols having the following formula: R—OH, wherein R is a $C_{1-6}$ alkyl group, preferably a $C_{1-3}$ alkyl group, and carboxylic acids having the following formula: R—COOH, wherein R is a $C_{1-6}$ alkyl group, preferably a $C_{1-3}$ alkyl group. The alcohol and carboxylic acids can be non-branched or branched isomers. Specific, non-limiting examples of additives that can be used are methanol, ethanol, propanol, isopropanol, acetic acid, propionic acid, or combinations thereof. Examples of low molecular weight include, but are not limited to, a molecular weight of about 20-80, preferably about 30-60.

Typical examples of low molecular weight, oxygen containing, monofunctional, organic additives and the zirconium polymer complex formed in a zirconium oxychloride solution are as follows:

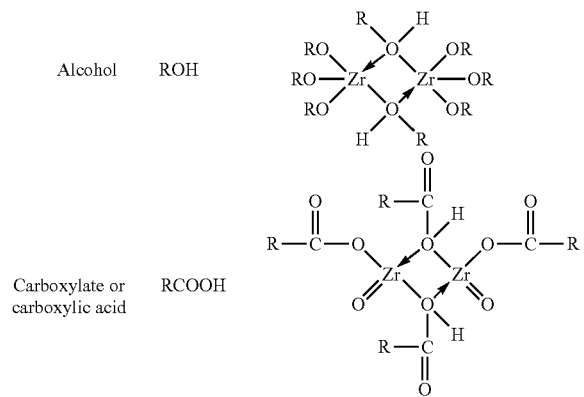

Alcohol ROH

Carboxylate or RCOOH
carboxylic acid

A solution wherein the low molecular weight, oxygen containing, monofunctional, organic additive forms a complex with zirconium ions can be formed by adding the additive to a solution containing zirconium oxychloride or by adding zirconium oxychloride to a solution containing the additive. In other words, the order of addition of the additive and the zirconium oxychloride to an aqueous solvent is not critical.

The properties of zirconium phosphate particles obtained by sol gel precipitation can optionally be altered by adjusting the pH of the phosphoric acid solution used. For example, the precipitating agent used in the method of the present invention can be orthophosphoric acid that is titrated with a base, like NaOH, to a pH of from about 1 to about 4. The partially titrated phosphoric acid can lower the acidity of the sol gel ZrP and thereby reduce the water of hydration. Otherwise, lattice $H^+$ can combine with $H_2O$ to form hydronium ions. Thus, carrying out sol gel precipitation at a higher pH of phosphate helps to promote the hardening of the ZrP gel. However, carrying out the precipitation reaction at an alkaline pH is less preferred because zirconium phosphate precipitated by alkaline phosphate can have poor ammonia adsorption properties. This technique can be carried out in conjunction with the use of at least one low molecular weight, oxygen containing, monofunctional, organic additive, as described above.

The present invention also relates in part to a method of synthesizing zirconium phosphate particles by sol gel precipitation wherein the particle size and/or particle size distribution of the zirconium phosphate particles obtained are controlled by controlling the rate at which the organic additive-containing solution of zirconium oxychloride is added to the reaction vessel, the rate at which the solution of phosphoric acid is added to the reaction vessel, the concentration of reactants, e.g., zirconium oxychloride, organic additive, phosphoric acid, and/or hydrochloric acid in the reaction vessel, and/or the speed and manner of agitation of the reaction mixture. In particular, it has been found that the particle size obtained by sol gel precipitation can be partly dependent upon the concentration of the reactants. When a solution of zirconium oxychloride is added to a solution of phosphoric acid, the concentration of phosphoric acid decreases as the reaction proceeds, leading to the possible formation of increasingly smaller particles. As a result, an undesirably wide range of particle sizes may be produced. To prevent this from possibly happening, both reactants, i.e., the additive-containing solution of zirconium oxychloride, and phosphoric acid, can optionally be added to a reaction vessel simultaneously (or nearly simultaneously) and the addition can be stretched out over a period of time, such as, for example, ten to thirty minutes or more, thereby allowing the concentration of phosphoric acid in the reaction solution to remain steady and controllable throughout the precipitation process. As a further example, a portion of a solution of phosphoric acid can be added to a reaction vessel, and the additive-containing solution of zirconium oxychloride and the remainder of the phosphoric acid solution can be added to the reaction vessel simultaneously at controlled rates, again allowing the concentration of phosphoric acid in the reaction solution to remain steady and controllable throughout the precipitation process.

In addition to the simultaneous addition of zirconium oxychloride and phosphoric acid solutions, other parameters, including the manner of addition of the zirconium oxychloride solution and the manner of mixing of the reactants, can be controlled to provide a more efficient reaction and to control the particle size range. For example, a spray head can be used as the inlet for the additive-containing solution of zirconium oxychloride so that the solution is added to the reaction vessel in the form of droplets, thereby providing a more efficient reaction. Further, the reaction vessel can be equipped to agitate the reactants as they are added to the reaction vessel and as the reaction proceeds, thereby providing for more efficient mixing and avoiding differences in particle sizes caused by differing concentrations of reactants in different sections of the reaction vessel. For example, the reaction vessel can include an agitator, such as, for example, an agitator having more than one set of blades attached to a shaft at different levels, so that the reactants in the reaction vessel are thoroughly mixed at all levels. As a particular example, a multi-impeller agitator can be used, such as an agitator that has three sets of blades, each set attached to a shaft at a different level. The use of an agitator to control or reduce agglomeration is optional. If an agitator is used, commercial agitators, including multi-impeller agitators, can be used. With a multi-impeller agitator, a low agitation speed, such as, for example 20-40 rpm, is preferred to avoid agglomeration without causing a break-up of gel particles. With a single-impeller agitator, a speed of about 60-70 rpm, for example, can be used. For any given agitator, the optimum speed is dependent on variables such as the tank size, shape, baffles, impeller size, and the like. Other methods of agitation or mixing can be used.

Appropriate process control methods can be used to ensure a suitable concentration range of reactants and flow rates for the precipitation process so that a desirable particle size range or distribution can be obtained. As an example, a desirable particle size range for zirconium phosphate particles to be used in a sorbent dialysis cartridge can be from about 20-80 microns, or from about 35-65 microns. Other particle size ranges can be used. To achieve this particle size distribution, and as an example, zirconium oxychloride solution containing isopropanol and a phosphoric acid solution can be formed as follows. The zirconium oxychloride solution can contain zirconium oxychloride at, or close to, its saturation point (for example, 500 g ZOC crystals in 375 mL water) since the size of polymeric units increases as the concentration increases. The amount of isopropanol can be the maximum amount (for example, about 300 g in the ZOC solution described herein) to provide the maximum reduction in the amount of coordinated water in the zirconium ion complex and suppress the degree of gelation. An excess amount of isopropanol can reduce the particle size too much by excessive emulsification, thereby producing many fine particles. An insufficient amount of isopropanol can result in an elevated degree of agglomeration and a higher percentage of particles in the larger size range (e.g., 80-120 microns). A typical solution of phosphoric acid can contain 516.5 g of 76% $H_3PO_4$+2.1 L water. The molar ratio of ZOC to phosphate or $H_3PO_4$ can be about 1:3±0.2.

A specific non-limiting example of a ZOC solution formulation is 500 g ZOC, 375 g water, 300 g isopropanol, and 70 g concentrated HCl. The molar ratio of ZOC to water to low molecular weight, oxygen containing, monofunctional, organic additive can be about 1:0.75:0.6. Another specific non-limiting example of a ZOC solution formulation is 500 g ZOC, 375 g water, 260 g glacial acetic acid, and 94 g concentrated HCl. The molar ratio of ZOC to water to low molecular weight, oxygen containing, monofunctional, organic additive can be about 1:0.75:0.52. The amounts given for the typical solution can, of course, be scaled up or down by maintaining the same proportion of reactants. Particle size control for use in sorbent dialysis cartridges can also be achieved by additional milling, if necessary, to meet cartridge performance requirements.

The flow rate for the phosphoric acid solution can be 80-100 ml/min for an addition time of 25-30 minutes, and the flow rate of the additive-containing solution of zirconium oxychloride can be 25-50 ml/min for an addition time of 15-30 minutes. The flow rate is provided for the solution described above and can be scaled up or down if a different amount of reactants is used. A higher flow rate of the phosphoric acid can increase its steady state concentration in the reaction bath and/or produces harder stable crystalline ZrP particles. Conversely, a lower flow rate can produce a more fragile product. As a specific example, the addition time of the reactants can be 30 minutes. Other flow rates and times can be used.

The sol gel zirconium phosphate particles in a slurry formed by a method according to the present invention can be stabilized by an immediate titration to raise the pH of the slurry. For example, the slurry can be titrated with a base, such as 50% NaOH, to bring the pH up to a range of about 1-2. (Typically, the pH of the slurry when formed is close to 0.1) Then, after allowing the zirconium phosphate particles to settle and harden further, the slurry can be titrated slowly to a higher pH, such as pH 5.5 or pH 6 to obtain the finished product. The partial titration provides an immediate reduction in the acidity of the material, which may otherwise induce the adsorption of water of hydration (since lattice $H^+$ can combine with $H_2O$ to form hydronium ions) and a softening of the gel. The advantage to performing the titration slowly and in stages is that the rapid addition of alkali can cause the rapid formation of water within the gel particles, which can burst the particles and produce an excessive number of fines. For the specific use of zirconium phosphate particles in sorbent dialysis cartridges, the second titration is preferable to a pH of 5.5 to obtain the optimum $Na^+$ content in the product due to the presence of $Na^+$ and $PO_4$ ions already present in the slurry.

Because sol gel precipitation in the phosphate concentration range used in the present invention tends to be a fast reaction, the techniques described above can be carried out without additional heating. However, a thermal treatment carried out with water may be helpful to improve the molecular structure of the zirconium phosphate particles by enhancing crystallinity. Thermal treatment may improve the crystal structure of ZrP by promoting an oxolation reaction as follows:

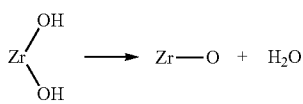

and by aiding the release of ionic impurities from the zirconium phosphate lattice formed in the sol gel precipitation. As an example of how the thermal treatment can be carried out, after zirconium phosphate has been formed by sol gel precipitation, the reaction slurry can be filtered and washed to remove chloride, excessive phosphoric acid, sulfate and additive chemicals. The filter cake obtained by filtration can then be transferred to a bath of deionized water (or RO water) and the slurry can be agitated for a short time (first wash). The filtration and washing can be repeated, for instance, until the total dissolved solids level (TDS level) in slurry is below 1200 ppm. The filter cake can be transferred to a bath of deionized water (or RO water) in a heating vessel equipped with an agitator and, with a moderate agitation speed, the slurry can be heated at moderate rate to about 180-185° F. (about 82-85° C.) with the temperature maintained in this range for 1 hour or longer. Then, the heated slurry can be allowed to cool to room temperature and the volume can be adjusted with water. Thereafter, the slurry can be titrated from a starting pH of about 1.8 to a desired pH, such as a pH of 5.75; pH 6; or pH 6.25 (or ranges therebetween) with a base, such as 50% NaOH, to obtain ZrP products of different $Na^+$ contents and acidity. The titrated ZrP can then be washed and filtered repeatedly with deionized water (or RO water) until the TDS level in the slurry is below 500 ppm. The filter cake after the final wash can then be transferred to a tray dryer and the titrated product can be dried to 14-18% loss on drying by moisture balance (LOD) at a temperature of about 160°-180° F. (71°-81° C.). The final product can be in the form of free-flowing powder, for instance, in a target particle size range of 30-60 µM and can be without agglomeration (or less than 1% by weight).

The following examples are given to illustrate the nature of the invention. It should be understood, however, that the present invention is not to be limited to the specific conditions or details set forth in these examples.

EXAMPLES

Example 1

Preparation of ZrP Particles by Sol Gel Precipitation

Solution A was prepared as follows: 20 g ZOC crystals was dissolved in 15 ml deionized water and 15 ml isopropanol was added to the solution. Then, with agitation by magnetic stirrer or plastic impeller, about 100 drops of concentrated HCl was added to the solution with continued agitation until all precipitate was redissolved to form a clear solution.

Solution B was prepared as follows: 30 g Technical Grade phosphoric acid (76%) was diluted in 60 ml water in a 500 ml beaker. With a magnetic stirrer, the diluted acid was heated to a boiling temperature.

Reaction process steps:

Step 1: Solution A was pumped into Solution B at boiling temperature at about 10 ml/min flow rate, with moderate agitation speed using magnetic stirrer or plastic impeller.

Step 2: After addition was complete to produce a slurry of precipitate, the slurry was heated for one hour to evaporate off the alcohol completely and improve crystal structure of the AZP precipitate.

Step 3: After heating for one hour, the slurry was allowed to cool. The precipitate was then filtered and washed with deionized water to remove excessive unreacted phosphoric acid.

Step 4: The washed product was dried in an oven at 180° F. until the moisture level was 5-20 weight percent LOD to form a free-flowing powder. The particle size was in a range of from 25-45 microns.

Example 2

Example 1 was repeated but the acid zirconium phosphate (AZP) product was titrated to pH 6.0 with 50% NaOH in about 200 ml deionized water and followed by washing before filtration and drying of the filtered product.

Example 3

The mixing process of ZOC/isopropanol and phosphoric acid in Example 1 was performed again at the ambient temperature of the acid. The $NH_4^+$—N adsorption capacity of the final product was about the same as the product obtained by high temperature mixing although there was some degree of agglomeration upon drying of the product.

Example 4

ZrP with particle size in the range 2-10 microns was obtained by grinding the final dried product of Example 1 or by modifying the formulation of the ZOC solution as follows before adding to the heated phosphoric acid and mixing with vigorous agitation:

ZOC Solution Formulation (Solution A):

| | |
|---|---|
| ZOC solid | 20 gm |
| Deionized water | 15 ml |
| Isopropanol | 30 ml |
| Conc. HCl | 0 drops |

The $NH_4^+$—N adsorption capacity of the fine particle size product was found to increase by about 10-20% over that of the normal particle size range (25-65 microns).

Example 5

A scale-up batch for Example 1 was made by adjusting the solution formulations (Solution A and Solution B) and the process parameters were as follows:

| Solution A | ZOC solid | 500 gm |
| | Deionized water | 375 ml |
| | Isopropanol | 375 ml or 300 gm |
| | Conc. HCl | 70 gm |
| Solution B | 76% $H_3PO_4$ | 550 gm |
| | Deionized water | 2.2 L |

(NOTE: Molar mixing ratio of ZOC:$H_3PO_4$ = about 1:2.92)

Reaction process steps:
Step 1: Solution A was pumped into Solution B at boiling temperature at about 25-30 ml/min flow rate for an addition time of 25-30 minutes, with moderate agitation speed (about 80 RPM) using plastic impeller.
Step 2: After addition was complete to produce a slurry of precipitate, the slurry was heated for 30 minutes to evaporate the alcohol completely and improve the crystal structure of the AZP precipitate.
Step 3: After heating for 30 minutes, the slurry was allowed to cool. The precipitate was then filtered and washed with deionized water to remove excessive unreacted phosphoric acid.
Step 4: The filter cake was transferred to about 3 L deionized water and agitated at mild speed to form a slurry, which was then titrated to a pH 6.0 by 50% NaOH. The titrated ZrP was then filtered and rewashed until the TDS in filtrate was about 500 PPM.
Step 5: The washed product was dried in an oven at 180° F. until the moisture level was about 5-20 weight percent LOD to form a free-flowing powder. The particle size was in the range of 35-65 microns.

The $NH_4^+$—N adsorption capacity of the product was the same as the small sample test in Example 1.

Example 6

Example 1 was repeated using acetic acid as organic additive in place of isopropanol with the ZOC solution formulation as follows (Solution A):

| ZOC solid | 20 gm |
| Deionized water | 15 ml |
| Glacial acetic acid | 15 ml |
| Conc. HCl | 200 drops |

The same amount and concentration of phosphoric acid at boiling temperature were used as in Example 1. The product was excessively washed with deionized water to remove residual acetic acid then titrated to pH 6.0. The same particle size ZrP product (35-65 microns) without agglomeration upon drying was obtained although $NH_4^+$—N adsorption capacity was slightly lower than that made by using isopropanol.

Example 7

Example 6 was repeated but the ZOC/acetic acid solution (Solution A) was added to the phosphoric acid at ambient temperature. The product was excessively washed with deionized water to remove residual acetic acid. One-half of the product was titrated to pH 6.0 while the other half remained untitrated. It was shown that all ZrP products had the same $NH_4^+$—N adsorption capacity as Example 6 regardless of mixing temperature and pH titration of product although the product obtained at ambient temperature of mixing had some degree of agglomeration upon drying.

Example 8

A scale-up batch for Example 7 at ambient temperature of mixing was made by adjusting the solution formulations (Solution A and Solution B) as follows:

| Solution A | ZOC solid | 500 gm |
| | Deionized water | 375 ml |
| | Glacial acetic acid | 250 ml or 260 gm |
| | Conc. HCl | 94 gm |
| Solution B | 76% $H_3PO_4$ | 550 gm |
| | Deionized water | 2.2 L |

(NOTE: Molar mixing ratio of ZOC:$H_3PO_4$ = about 1:2.92)

An excessive amount of water was used to wash the product to remove residual acetic acid. The $NH_4^+$—N adsorption capacity of the titrated product was about the same as the small sample test in Example 7 although the product obtained at ambient temperature of mixing had some degree of agglomeration upon drying.

Example 9

The fine particle ZrP with particle size in the range 2-10 microns was obtained by grinding the final dried product of Example 6 or by modifying the formulation of the ZOC solution as follows before adding to the heated phosphoric acid and mixing with vigorous agitation:
ZOC Solution Formulation (Solution A):

| ZOC solid | 20 gm |
| Deionized water | 15 ml |
| Glacial acetic acid | 30 ml |
| Conc. HCl | 0 drops |

The $NH_4^+$—N adsorption capacity of the fine particle size product was found to increase by about 10-20% over that of the normal particle size range (25-65 microns).

Example 10

ZrP Particles Having Enhanced Ammonium Adsorption Capacity

ZrP particles were prepared by a sol gel method according to the present invention, by the sol gel method according to U.S. Patent Application Publication No. 2006/0140840 (Example 2 using glycerol and sodium sulfate as the additive), and from basic zirconium sulfate (BZS) by a (non-sol gel) method prepared as follows: one (1) kg of BZS was added to deionized water in a reactor to form a slurry with moderate agitation speed. Then, about 770 ml Technical Grade phosphoric acid (76%) diluted with equal volume of water was pumped into the slurry. With slow agitation, the slurry was heated at moderate or maximum rate to 180-185° F., and then heated to maintain that temperature for one hour after the temperature was reached. The slurry was then cooled to room temperature. The product was filtered and washed in a Buchnell funnel with deionized water. The filter cake was then dried in a tray dryer at 180° F. until the moisture level was 12-18 weight percent LOD. The particle size was in a range of from 25-60 microns.

The $NH_4^+$—N adsorption capacity was measured at three $NH_4^+$—N exposed concentrations and the results were compared. The results, shown in Table 1, confirm that ZrP particles prepared according to the present invention exhibit increased $NH_4^+$—N adsorption compared to particles prepared by the previous methods.

TABLE 1

| Type of ZrP | Exposed $NH_4^+$—N concentration | $NH_4^+$—N adsorption per g ZrP (capacity in presence of Na) | Capacity in Water |
|---|---|---|---|
| Sol gel ZrP according to present invention (Example 1) | 5 mg/dL | 4.95 mg $NH_4^+$—N/g | |
| | 10 mg/dL | 7.76 mg $NH_4^+$—N/g | 25 mg/gm |
| | 20 mg/dL | 11.84 mg $NH_4^+$—N/g | 38 mg/gm |
| Sol gel ZrP according to U.S. Patent Application Publication No. 2006/0140840 | 5 mg/dL | 2.23 mg $NH_4^+$—N/g | |
| | 10 mg/dL | 3.74 mg $NH_4^+$—N/g | |
| | 20 mg/dL | 7.60 mg $NH_4^+$—N/g | |
| ZrP made from BZS | 5 mg/dL | 2.00 mg $NH_4^+$—N/g | |
| | 10 mg/dL | 3.58 mg $NH_4^+$—N/g | |
| | 20 mg/dL | 6.515 mg $NH_4^+$—N/g | |

Example 11

Grinding the ZrP product (e.g., ZrP of Example 1) to fine particle size after drying can increase the $NH_4^+$ adsorption capacity from 28 mg $NH_4^+$—N/gm to 36 mg $NH_4$—N/gm at the $NH_4^+$—N concentration of 20 mg/dL in water (~28%). The adsorption isotherms after grinding in comparison with ZrP made from BZS can be shown by the Table below:

TABLE 2

| | $NH_4^+$—N concentration | Capacity in the $NaHCO_3$/NaCl dialysate | Adsorption isotherm |
|---|---|---|---|
| Sol gel ZrP | 10 mg/dL | 8 mg/gm | $NH_4^+$—N adsorption capacity (mg/gm ZrP) = $7.16 + 0.15 \times [NH_4^+\text{—N}]$ r = 0.9878 |
| | 20 mg/dL | 11.3 mg/gm | |
| | 55 mg/dL | 15 mg/gm | |
| | 85 mg/dL | 19 mg/gm | |
| | 100 mg/dL | 23 mg/gm | |

TABLE 2-continued

| | $NH_4^+$—N concentration | Capacity in the $NaHCO_3$/NaCl dialysate | Adsorption isotherm |
|---|---|---|---|
| Current ZrP made from BZS | 10 mg/dL | 4.2 mg/gm | $NH_4^+$—N adsorption capacity (mg/gm ZrP) = $3.38 + 0.137 \times [NH_4^+\text{—N}]$ r = 0.99 |
| | 20 mg/dL | 7.12 mg/gm | |
| | 55 mg/dL | 10.2 mg/gm | |
| | 85 mg/dL | 15.4 mg/gm | |
| | 100 mg/dL | 17.1 mg/gm | |

Other typical $NH_4^+$—N adsorption capacity data in water in variation with organic additives (isopropanol, acetic acid, tartaric acid, glycerol, polyvinyl alcohol); temperature of mixing (ambient vs. boiling temperature); ZrP pH (ZrP pH 6.0 vs. untitrated ZrP); and particle size (35-65 microns vs. ground ZrP fine powder, 2-10 microns) are summarized in the Table as shown below: (NOTE: Moisture level data was not taken because it is found that sol gel ZrP can be dried to very low moisture level without affecting the $NH_4^+$—N adsorption capacity).

TABLE 3

| Organic additive | Temperature of mixing | ZrP pH | Particle size | $NH_4^+$—N adsorption capacity in water mg/gm ZrP |
|---|---|---|---|---|
| Isopropanol | ambient | untitrated | ground ZrP fine powder 2-10 microns | at 10 mg/dL $NH_4^+$—N conc. 28.89 mg/gm |
| | | | | at 20 mg/dL $NH_4^+$—N conc. 36.21 mg/gm |
| | boiling | untitrated | ground ZrP fine powder 2-10 microns | at 10 mg/dL $NH_4^+$—N conc. 26.9 mg/gm |
| | | | | at 20 mg/dL $NH_4^+$—N conc. 34.76 mg/gm |
| | boiling | untitrated | 35-65 microns | at 10 mg/dL $NH_4^+$—N conc. 25.53 mg/gm |
| | | | | at 20 mg/dL $NH_4^+$—N conc. 31.83 mg/gm |
| | boiling | pH 6.0 | ground ZrP fine powder 2-10 microns | at 10 mg/dL $NH_4^+$—N conc. 24.9 mg/gm |
| | | | | at 20 mg/dL $NH_4^+$—N conc. 38.4 mg/gm |
| | boiling | pH 6.0 | 35-65 microns | at 10 mg/dL $NH_4^+$—N conc. 24.66 mg/gm |
| | | | | at 20 mg/dL $NH_4^+$—N conc. 32.19 mg/gm |
| | boiling | pH 4.0 | 35-65 microns | at 10 mg/dL $NH_4^+$—N conc. 27.54 mg/gm |
| | | | | at 20 mg/dL $NH_4^+$—N conc. 33.45 mg/gm |
| acetic acid | ambient | untitrated | ground ZrP fine powder 2-10 microns | at 10 mg/dL $NH_4^+$—N conc. 25.95 mg/gm |
| | | | | at 20 mg/dL $NH_4^+$—N conc. 35.7 mg/gm |
| | ambient | untitrated | 35-65 microns | at 10 mg/dL $NH_4^+$—N conc. 24.96 mg/gm |
| | | | | at 20 mg/dL $NH_4^+$—N conc. 27.3 mg/gm |
| | ambient | pH 6.0 | 35-65 microns | at 10 mg/dL $NH_4^+$—N conc. 25.65 mg/gm |
| | | | | at 20 mg/dL $NH_4^+$—N conc. 28.95 mg/gm |
| | boiling | pH 6.0 | 35-65 microns | at 10 mg/dL $NH_4^+$—N conc. 25.45 mg/gm |
| | | | | at 20 mg/dL $NH_4^+$—N conc. 26.64 mg/gm |
| no organic additive; just conc. HCl alone | ambient | untitrated | ground ZrP fine powder 2-10 microns (partial gelation) | at 10 mg/dL $NH_4^+$—N conc. 21.47 mg/gm |
| | | | | at 20 mg/dL $NH_4^+$—N conc. 27.31 mg/gm |
| | Boiling | pH 6.0 | 35-65 microns | at 10 mg/dL $NH_4^+$—N conc. 20.27 mg/gm |
| | | | | at 20 mg/dL $NH_4^+$—N conc. 24.2 mg/gm |
| Glycerol | Boiling | pH 6.0 | 35-65 microns | at 10 mg/dL $NH_4^+$—N conc. 6.46 mg/gm |
| | | | | at 20 mg/dL $NH_4^+$—N conc. 9.98 mg/gm |

TABLE 3-continued

| Organic additive | Temperature of mixing | ZrP pH | Particle size | $NH_4^+$—N adsorption capacity in water mg/gm ZrP |
|---|---|---|---|---|
| polyvinyl alcohol | Boiling | pH 5.0 | 35-65 microns | at 10 mg/dL $NH_4^+$—N conc. 3.92 mg/gm<br>at 20 mg/dL $NH_4^+$—N conc. 5.39 mg/gm |
| tartaric acid | Boiling | pH 6.0 | 35-65 microns | at 10 mg/dL $NH_4^+$—N conc. 2.76 mg/gm<br>at 20 mg/dL $NH_4^+$—N conc. 3.43 mg/gm |

Example 12

A lab-scale parametric study of the sol gel process for preparation of ZrP particles was performed for various parameters, including, for example, type and amount of additive to ZOC solution, reactant mixing method, phosphoric acid amount, hydrothermal treatment of crude sol gel, HCl amount, and particle size. Comparison gels comprising ZrP prepared with an inorganic oxygen additive ($Na_2CO_3$ (soda ash)), and ZrP made from BZS, were included in this study. Some of the product particles were analyzed for one or more of adsorption capacity, BET surface area, pore volume, pore size distribution, and/or gel swelling property. For purposes of this example, reverse osmosis (RO) water can be substituted for deionized (DI) water where referenced.

Method Steps:

Step 1: Preparation of ZOC Solution with Additive (Solution A)

Solution A was prepared with an additive selected from alcohol (isopropanol or 95% methanol), acetic acid, or soda ash. These types of solutions are designated Solutions A1, A2, and A3.

Solution A1 was prepared as follows: 500 g ZOC crystals was dissolved in 375 ml deionized (DI) water with agitation, and 200 ml glacial acetic acid is transferred to the ZOC solution and agitated until the solution mixture was completely clear. (NOTE: About 50 gm conc. HCl optionally can be added to the ZOC solution first before the mixing with acetic acid if a larger particle size is desired. Agitation to re-dissolve any precipitate thus formed until the solution is clear).

Solution A2 was prepared as follows: 500 g ZOC crystals was dissolved in 375 ml deionized water with agitation, and 300 ml (isopropanol or 95% methanol) is transferred to the ZOC solution and agitated until the solution mixture was completely clear. (NOTE: Addition of conc. HCL to improve particle size is optional as in Solution A1).

Solution A3 was prepared as follows: 500 g ZOC crystals was dissolved in 250 ml deionized water with agitation (totally or partially), and 40 g soda ash was dissolved in 125 mL deionized water in another vessel with agitation (totally or partially). The soda ash solution (totally or partially dissolved) was transferred to the ZOC solution and agitated until the solution mixture is completely clear. (NOTE: Addition of conc. HCl also is optional as in Solutions A1 and A2). The resultant solution was used at once or within a short time for the sol gel ZP synthesis.

Step 2: Preparation of Phosphoric Acid Used for Reaction (Solution B)

Solution B was prepared as follows: 600 g Technical Grade phosphoric acid (76%) was diluted in 500 deionized mL water and mixed with agitation.

Step 3: Precipitation reaction of sol gel ZP by simultaneous addition of ZOC and $H_3PO_4$ a) Approximately 280 ml of the diluted phosphoric acid prepared in Step 2 was transferred to a 4 L reactor vessel and agitation was started at 240 RPM.

b) Solution A and Solution B were simultaneously pumped into the reactor vessel at ambient temperature at the flow rate of about 20 mL/min for both fluids such that the addition of the two fluids was complete simultaneously after about 30 minutes.

c) 500 mL deionized water was added to dilute the slurry and the agitation was continued until the sol gel ZP particles hardened.

Step 4: Washing of Crude Sol Gel ZP

The slurry of product from Step 3 was pumped into a vacuum batch filter and the filter cake was briefly washed with 6 L deionized water to remove the chloride. (NOTE: If hydrothermal treatment is not used in the following Step 5, Step 4 goes directly to removal of excessive $PO_4$ for pre-titration in Step 6 by continuing to wash the filter cake until the filtrate has TDS below 1200 ppm).

Step 5: Hydrothermal Treatment

The washed filter cake obtained from Step 4 was transferred into 3 L deionized water in the 4 L reactor vessel, and agitated at slow speed to form a slurry. 150 g 76% $H_3PO_4$ was added to the slurry and the resulting slurry was heated to a temperature at about 90° C., and maintained at that temperature or just below that temperature for one hour and then heating was stopped to allow the slurry to cool.

Step 6: Filtration/Washing to Remove Excessive $PO_4$ for Pre-Titration

The cooled slurry of Step 5 was pumped after the hydrothermal treatment to the vacuum batch filter. The filter cake was washed with deionized water until the filtrate has TDS below 1200 ppm.

Step 7: Filtration of Acid Sol Gel ZP

The acid sol gel ZP filter cake was transferred after washing to a 6 L bath of deionized water and agitated mildly to form a slurry. The slurry was titrated to pH 6 by adding 50% NaOH.

Step 8: Final Washing and Drying

The slurry of Step 7 was pumped after titration to the vacuum batch filter. The washing of the filter cake was continued until the TDS of the filtrate is below 500 ppm. The filter cake was transferred to a tray dryer and the material was dried at a temperature of 100° F.-120° F. to the moisture level of 18-22% LOD. Continuous stirring of the material during drying was used to ensure uniform drying.

Step 9: Particle Size Control

The dried product was gently ground to a free-flowing powder to break up the soft agglomerates. The powder product was sieved and the portion was kept with the particle size in the ranges (45-90) microns or (45-180) microns for testing.

Product Quality-Material Testing: $NH_4^+$—N Adsorption Quality

The $NH_4^+$—N adsorption quality of the sol gel ZP samples were tested according to the procedure as follows:

1 gm of sample was shaken in 300 ml of $(NH_4)_2CO_3$ solution in deionized water for 5 minutes at concentrations of (a) 20 mg/dL $NH_4^+$—N; (b) 30 mg/dL $NH_4^+$—N. (NOTE:

Some sample tests were repeated by using $(NH_4)_2CO_3$ solution in dialysate (105 mEq/L NaCl; 35 mEq/L NaHCO$_3$). Filtering with Whatman #42 was done afterwards and residual $NH_4^+$—N concentration was analyzed by Indophenate Test to calculate adsorption capacity of the sample.

The results for $NH_4^+$—N adsorption quality determinations for various sol gel ZP samples representing embodiments of the present invention and comparison or control sol gel ZP samples are indicated in Table 4. Table 4 comprises the indicated parts 4A-4J. "Mic" is microns.

TABLE 4

| | Parameters | | | | | | Adsorption Quality | |
|---|---|---|---|---|---|---|---|---|
| Additive | Method of Mixing | Particle Size | Hydrothermal Treatment | Conc. HCl | 75% H$_3$PO$_4$ | Sample No. | Capacity at $NH_4^-$N conc. Of | |
| | | | | | | | 20 mg/dL | 30 mg/dL |
| 4A: Parametric Variation: Simultaneous Addition of ZOC and H$_3$PO$_4$ | | | | | | | | |
| 375 ml isopropanol | Simultaneous add | <200 mic >45 mic | No hydrothermal treatment | 50 gm | 600 gm | 1 | 39.16 mg per gm | 41.15 mg per gm |
| 375 ml isopropanol (overdried 11.6% LOD) | Simultaneous add | <200 mic >45 mic | Hydrothermal treatment with 100 gm phosphoric acid | 50 gm | 600 gm | 2 | 35.84 mg per gm | 38.13 mg per gm |
| 375 ml isopropanol | Simultaneous add | <200 mic >45 mic | Hydrothermal treatment with 100 gm phosphoric acid | 50 gm | 600 gm | 3 | 38.53 mg per gm | 42.21 mg per gm |
| 240 ml acetic acid | Simultaneous add | <90 mic >45 mic | Hydrothermal treatment with 100 gm phosphoric acid | 50 gm | 600 gm | 4 5 | 40 mg per gm 39.31 mg per gm | 43.23 mg per gm 44.26 mg per gm |
| 375 ml isopropanol | Simultaneous add | <90 mic >45 mic | No hydrothermal treatment | 50 gm | 600 gm | 6 | 40 mg per gm | 45.26 mg per gm |
| 300 ml acetic acid | Simultaneous add | <90 mic >45 mic | No hydrothermal treatment | 50 gm | 600 gm | 7 | 36.42 mg per gm | 44.31 mg per gm |
| 375 ml 95% methanol | Simultaneous add | <90 mic including fines | No hydrothermal treatment | 50 gm | 600 gm | 8 | 35.29 mg per gm | 41.21 mg per gm |
| 375 ml 95% methanol | Simultaneous add | <90 mic >45 mic | Hydrothermal treatment with 150 gm phosphoric acid | 50 gm | 600 gm | 9 | 37.48 mg per gm | 45.36 mg per gm |
| 150 ml acetic acid | Simultaneous add | <90 mic >45 mic | No hydrothermal treatment | 50 gm | 600 gm | 10 | 37.56 mg per gm | 43.45 mg per gm |
| 150 ml 95% methanol | Simultaneous add | <90 mic >45 mic | No hydrothermal treatment | 50 gm | 600 gm | 11 | 34.611 mg per gm | 37.91 mg per gm |
| 150 ml 95% methanol | Simultaneous add | <90 mic >45 mic | No hydrothermal treatment | 50 gm | 500 gm | 12 | 32.9 mg per gm | 42.2 mg per gm |
| 150 ml acetic acid | Simultaneous add | <90 mic >45 mic | Hydrothermal treatment in presence of 150 gm H$_3$PO$_4$ | 0 gm | 800 gm | 13 | 40.14 mg per gm | 49.1 mg per gm |
| 4B: Parametric Variation: Acetic Acid as Additive | | | | | | | | |
| 200 ml acetic acid | Sequential add | <840 mic >45 mic | No hydrothermal treatment | 50 gm | 600 gm | 14 15 | 31.89 mg per gm 34.59 mg per gm | 41.16 mg per gm 36.70 mg per gm |
| 300 ml acetic acid | Sequential add | <90 mic >45 mic | Hydrothermal treatment with 150 gm H$_3$PO$_4$ | 0 gm | 600 gm | 16 | 40.38 mg per gm | 46.48 mg per gm |
| 200 ml acetic acid | Sequential add | <90 mic >45 mic | Hydrothermal treatment with 150 gm H$_3$PO$_4$ | 0 gm | 600 gm | 17 | 40.87 mg per gm | 49.3 mg per gm |
| 150 ml acetic acid | Sequential add | <90 mic >45 mic | HHydrothermal treatment with 150 gm H$_3$PO$_4$ | 50 gm | 600 gm | 18 | 37.29 mg per gm | 37.78 mg per gm |
| 370 ml acetic acid | Sequential add | <90 mic >45 mic | Hydrothermal treatment with 50 gm H$_3$PO$_4$ | 50 gm | 600 gm | 19 | 43.07 mg per gm | — |
| 4C: Parametric Variation: Amount of Phosphoric Acid | | | | | | | | |
| 375 ml isopropanol | Sequential add | <90 mic >45 mic | High temp precip and continuous heating | 50 gm | 600 gm | 20 21 | 37.1 mg per gm 38.2 mg per gm | — |
| 375 ml isopropanol | Sequential add | <90 mic >45 mic | High temp precip and continuous heating | 50 gm | 570 gm | 22 | 34.16 mg per gm | — |
| 375 ml isopropanol | Sequential add | <90 mic >45 mic | High temp precip and continuous heating | 50 gm | 550 gm | 23 | 44 mg per gm | — |
| 375 ml isopropanol | Sequential add | <90 mic >45 mic | High temp precip and continuous heating | 50 gm | 500 gm | 24 | 38.98 mg per gm | — |
| 375 ml isopropanol | Sequential add | <90 mic >45 mic | High temp precip and continuous heating | 50 gm | 300 gm | 25 | 33.78 mg per gm | — |
| 375 ml isopropanol | Sequential add | <840 mic >90 mic | Hydrothermal treatment with 150 gm H$_3$PO$_4$ | 50 gm | 450 gm | 26 | 32.04 mg per gm | 41.14 mg per gm |
| 150 ml 95% methanol | Simultaneous add | <90 mic >45 mic | No hydrothermal treatment | 50 gm | 500 gm | 12 | 32.9 mg per gm | 42.2 mg per gm |
| 150 ml acetic acid | Simultaneous add | <90 mic >45 mic | Hydrothermal treatment in presence of 150 gm H$_3$PO$_4$ | 0 gm | 800 gm | 13 | 40.13 mg per gm 41.06 mg per gm | 49.11 mg per gm 46.84 mg per gm |
| 250 ml acetic acid | Simultaneous add | <90 mic >45 mic | Hydrothermal treatment in presence of 150 gm H$_3$PO$_4$ | 0 gm | 1000 gm (2.6 L water) | 27 | 39.24 mg per gm | 42.29 mg per gm |

TABLE 4-continued

| Parameters | | | | | | Adsorption Quality | | |
|---|---|---|---|---|---|---|---|---|
| Additive | Method of Mixing | Particle Size | Hydrothermal Treatment | Conc. HCl | 75% $H_3PO_4$ | Sample No. | Capacity at $NH_4^-N$ conc. Of | |
| | | | | | | | 20 mg/dL | 30 mg/dL |
| 250 ml acetic acid | Simultaneous add | <90 mic >45 mic | Hydrothermal treatment in presence of 150 gm $H_3PO_4$ | 0 gm | 1200 gm (1.8 L water) | 28 | 39.24 mg per gm | 41.1 mg per gm |
| 250 ml acetic acid | Simultaneous add | <90 mic >45 mic | Hydrothermal treatment in presence of 150 gm $H_3PO_4$ | 0 gm | 1400 gm (1 L water) | 29 | 40.80 mg per gm | 49.18 mg per gm |
| | | | 4D: Parametric Variation: Titrated ZP vs. Untitrated ZP | | | | | |
| 300 ml isopropanol | Sequential add | <90 mic >45 mic | Hydrothermal treatment with no $H_3PO_4$ | 65 gm | 600 gm | 30 | 30.1 mg per gm untitrated | — |
| 250 ml isopropanol | Sequential add | <90 mic >45 mic | Hydrothermal treatment with no $H_3PO_4$ | 50 gm | 600 gm | 31 | 30.63 mg per gm untitrated | — |
| 200 ml isopropanol | Sequential add | <90 mic >45 mic | Hydrothermal treatment with no $H_3PO_4$ | 50 gm | 600 gm | 32 | 32.86 mg per gm untitrated | — |
| 300 ml isopropanol | Sequential add | <90 mic >45 mic | High temp precip and continuous heating | 70 gm | 600 gm | 33, 34 | 28.6 mg per gm untitrated | — |
| | | | 4E: Parametric Variation: Amount of Phosphoric Acid Used for Hydrothermal Treatment | | | | | |
| 300 ml isopropanol | Sequential add | <90 mic >45 mic | Hydrothermal treatment with no additional $H_3PO_4$ | 65 gm | 600 gm | 35 | 32 mg per gm | — |
| 350 ml isopropanol | Sequential add | <90 mic >45 mic | Hydrothermal treatment with 50 gm $H_3PO_4$ | 50 gm | 600 gm | 36 | 35 mg per gm | — |
| 350 ml isopropanol | Sequential add | <90 mic >45 mic | Hydrothermal treatment with 100 gm $H_3PO_4$ | 50 gm | 600 gm | 37 | 44 mg per gm | — |
| 350 ml isopropanol | Sequential add | <90 mic >45 mic | Hydrothermal treatment with 150 gm $H_3PO_4$ | 50 gm | 600 gm | 38 | 48.37 mg per gm | — |
| | | | 4F: Parametric Variation: Room Temp Precip. With & Without Post-Hydrothermal Treatment vs. High Temp Precip. & Continuous Heating | | | | | |
| 375 ml isopropanol | Sequential add | <840 mic >45 mic | Room temp precip and no hydrothermal treatment | 50 gm | 600 gm | 39 40 41 | 36.07 mg per gm 30.55 mg per gm 35.01 mg per gm | 40.20 mg per gm 40.48 mg per gm 40.23 mg per gm |
| 375 ml isopropanol | Sequential add | <90 mic >45 mic | Hydrothermal treatment with 150 gm phosphoric acid | 50 gm | 600 gm | 42 43 44 | 44.75 mg per gm 43.46 mg per gm 42.05 mg per gm | 58.61 mg per gm 47.22 mg per gm 47.56 mg per gm |
| 375 ml isopropanol | Sequential add | <840 mic >45 mic | Hydrothermal treatment with 150 gm phosphoric acid | 50 gm | 600 gm | 45 46 47 | 36.05 mg per gm 38.28 mg per gm 37.07 mg per gm | 43.43 mg per gm 45.36 mg per gm 45.81 mg per gm |
| 375 ml isopropanol | Sequential add | <90 mic >45 mic | High temp precip and continuous heating | 50 gm | 600 gm | 32A 31A 48 30A 35A 49 50 51 21 20 | 32.86 mg per gm 30.63 mg per gm 37.02 mg per gm 30.10 mg per gm 32.00 mg per gm 30.15 mg per gm 30.40 mg per gm 29.75 mg per gm 38.20 mg per gm 37.10 mg per gm | N/A |
| | | | 4G: Parametric Variation: Amount of Isopropanol | | | | | |
| 350 ml isopropanol | Sequential add | <90 mic >45 mic | Hydrothermal treatment with 150 gm $H_3PO_4$ | 50 gm | 600 gm | 52 | 36.88 mg per gm | 48.44 mg per gm |
| 300 ml isopropanol | Sequential add | <90 mic >45 mic | Hydrothermal treatment with no add $H_3PO_4$ | 50 gm | 600 gm | 48 | 37.02 mg per gm | — |
| 250 ml isopropanol | Sequential add | <90 mic >45 mic | Hydrothermal treatment with no add $H_3PO_4$ | 50 gm | 600 gm | 31B | 37.52 mg per gm | — |
| 200 ml isopropanol | Sequential add | <90 mic >45 mic | Hydrothermal treatment with 150 gm $H_3PO_4$ | 50 gm | 600 gm | 53 | 34.13 mg per gm | 41.85 mg per gm |
| | | | 4H: Parametric Variation: Using Soda Ash as Additive | | | | | |
| 40 gm soda ash | Simultaneous addition | <180 mic >45 mic | Hydrothermal treatment in presence of 150 gm $H_3PO_4$ | 0 gm | 600 gm | 54 | 36.49 mg per gm | 43.25 mg per gm |
| 40 gm soda ash | Simultaneous addition | <180 mic >45 mic | No hydrothermal treatment | 0 gm | 600 gm | 55 | 35.35 mg per gm | 37.95 mg per gm |
| 40 gm soda ash | Simultaneous addition | <180 mic >45 mic | No hydrothermal treatment | 0 gm | 600 gm | 56 | 39.91 mg per gm | 41.74 mg per gm |
| 30 gm soda ash | Simultaneous addition | <180 mic >45 mic | Hydrothermal treatment in presence of 150 gm $H_3PO_4$ | 0 gm | 600 gm | 57 | 38.42 mg per gm | 42.33 mg per gm |
| | | | 4I: Parametric Variation: Particle Size | | | | | |
| 375 ml isopropanol | Sequential add | <840 mic >45 mic | Hydrothermal treatment with 150 gm $H_3PO_4$ | 50 gm | 600 gm | 45 58 59 46 47 | 36.06 mg per gm 37.75 mg per gm 36.67 mg per gm 38.28 mg per gm 37.07 mg per gm | 43.43 mg per gm 47.74 mg per gm 43.14 mg per gm 45.36 mg per gm 45.81 mg per gm |

TABLE 4-continued

| | Parameters | | | | | | Adsorption Quality | |
|---|---|---|---|---|---|---|---|---|
| Additive | Method of Mixing | Particle Size | Hydrothermal Treatment | Conc. HCl | 75% $H_3PO_4$ | Sample No. | Capacity at $NH_4^+$-N conc. Of | |
| | | | | | | | 20 mg/dL | 30 mg/dL |
| 375 ml isopropanol | Sequential add | <90 mic >45 mic | Hydrothermal treatment with 150 gm $H_3PO_4$ | 50 gm | 600 gm | 43 | 43.46 mg per gm | 47.22 mg per gm |
| | | | | | | 44 | 42.05 mg per gm | 47.56 mg per gm |
| | | | | | | 42 | 44.75 mg per gm | 58.61 mg per gm |
| | | | | | | 60 | 37.95 mg per gm | 45.21 mg per gm |
| | | | | | | 61 | 38.30 mg per gm | 41.14 mg per gm |
| | | | | | | 62 | 38.34 mg per gm | 48.27 mg per gm |
| | | | | | | 63 | 48.90 mg per gm | 56.58 mg per gm |
| | | | | | | 38A | 48.37 mg per gm | 58.38 mg per gm |
| | | | | | | 64 | 41.71 mg per gm | 45.10 mg per gm |
| | | | | | | 65 | 43.47 mg per gm | 47.88 mg per gm |
| 375 ml isopropanol | Sequential add | <45 mic | Hydrothermal treatment with 150 gm $H_3PO_4$ | 50 gm | 600 gm | 66 | 40.99 mg per gm | 48.28 mg per gm |
| 4J: Repeat of Sample Adsorption Test in Dialysate (105 mEq/L NaCl, 35 mEq/L $NaHCO_3$) | | | | | | | | |
| Plant ZP Control | | | | | | 67 | 17.497 mg per gm | 19.612 mg per gm |
| 150 ml acetic acid | Simultaneous add | <90 mic >45 mic | Hydrothermal treatment in presence of 150 gm $H_3PO_4$ | 0 gm | 800 gm | 68 | 20.107 mg per gm | 24.77 mg per gm |
| 250 ml acetic acid | Simultaneous add | <90 mic >45 mic | Hydrothermal treatment in presence of 150 gm $H_3PO_4$ | 0 gm | 1400 gm | 69 | 20.044 mg per gm | 25.007 mg per gm |
| 40 gm soda ash | Simultaneous add | <180 mic >45 mic | Hydrothermal treatment in presence of 150 gm $H_3PO_4$ | 0 gm | 800 gm | 70 | 20.991 mg per gm | 28.193 mg per gm |

Product Quality-Cartridge Performance Test

The particles for some of the sol gel samples were evaluated for sorbent cartridge application based on $NH_4^+$—N adsorption capacity of the cartridge, and the flow resistance pressure as well as the leakage behavior of it, according to the procedure as follows.

The cartridge was assembled as shown in FIG. 1 by the following configuration using 800 gm of sol gel ZP in the REDY cartridge canister. In testing the $NH_4^+$—N capacity of the cartridge, it was first primed with 12 L dialysate (105 mEq/L NaCl; 35 mEq/L $NaHCO_3$). Afterwards, 54 L dialysate containing 50 mg/dL $NH_4^+$—N in the form of $(NH_4)_2CO_3$ was single passed through the cartridge to simulate the composition after hydrolysis of urea. The single pass flow rate of the solution was maintained at 250 ml/min until $NH_4^+$—N breaks through at the level above 2 mg/dL. The residual volume of the unused $(NH_4)_2CO_3$ solution was recorded and the $NH_4^+$—N adsorption capacity of the cartridge was calculated based on the following calculations:

$$NH_4^+\text{—N adsorption capacity of cartridge} = 0.5 \text{ gm } NH_4^+\text{—N/L} \times 0.25 \text{ L/min} \times \text{breakthrough time in min.} \quad (i)$$

$$0.5 \text{ gm } NH_4^+\text{—N/L} \times (54 \text{ L} - \text{residual volume in L}). \quad (ii)$$

The flow dynamics of the cartridge was examined by spraying the cross-section of the ZP layer with the $NH_4^+$ indicator solution to reveal the unused ZP used for $NH_4^+$—N adsorption. The $NH_4^+$—N capacity for the 800 gm ZP cartridge was re-calculated by taking into account the unused portion.

The results for cartridge tests for various sol gel ZP samples representing embodiments of the present invention and comparison with a BZS ZP sol gel as a control are indicated in Table 5.

TABLE 5

Cartridge Test Results Summary in Comparison with BZS ZP

| Test No. | Cartridge Design Features | ZP Quality and Preparation | $NH_4^+$—N Breakthrough Time | $NH_4^+$—N Adsorption Capacity at B.T. | % Unused ZP | Predicted UNCif ZP fully utilized | Flow resistance pressure |
|---|---|---|---|---|---|---|---|
| 1 (control) | 1 thin cellular sponge; blended with glass beads | Plant ZP | 195 min | 25.2 gm | 5% | 26.5 gm | 12.5 psi max |
| 2 | Regular packing | Particle size: <90μ Adsorption: 47 mg $NH_4^+$—N per gm Prep: isopropanol additive; sequential addition and hydrothermal treatment (Sol Gel ZP # 37, 60) | 135 min | 16.4 gm | 40% | 27 gm | 22 psi max |
| 3 | Regular packing | Particle size: <90μ Adsorption: 47 mg $NH_4^+$—N per gm Prep: isopropanol additive; sequential addition and hydrothermal treatment (Sol Gel ZP # 65, 64) | 128 min | 17 gm | 50% | 34 gm | >30 psi max |

TABLE 5-continued

Cartridge Test Results Summary in Comparison with BZS ZP

| Test No. | Cartridge Design Features | ZP Quality and Preparation | $NH_4^+$—N Breakthrough Time | $NH_4^+$—N Adsorption Capacity at B.T. | % Unused ZP | Predicted UNCif ZP fully utilized | Flow resistance pressure |
|---|---|---|---|---|---|---|---|
| 4 | Regular packing | Particle size: <90μ<br>Adsorption: 48 mg $NH_4^+$—N per gm<br>Prep: isopropanol additive; sequential addition and hydrothermal treatment<br>(Sol Gel ZP # 38A, 63) | 97 min | 12.5 gm | 55% | 28 gm | 31 psi max |
| 5 | ¾ inch air space above ZP layer | Particle size: <90μ<br>Adsorption: 45 mg $NH_4^+$—N per gm<br>Prep: acidic acid additive; sequential addition and hydrothermal treatment<br>(Sol Gel ZP # 17, 16) | 110 min | 13 gm | 70% | 43 gm | 9 psi max |
| 7 | ¼ inch air space above ZP layer | Particle size: <90μ<br>Adsorption: 45 mg $NH_4^+$—N per gm<br>Prep: isopropanol additive; sequential addition and hydrothermal treatment<br>(Sol Gel ZP # 42, 44) | 180 min | 20.7 gm | 20% | 26 gm | 21.5 psi max |
| 8 | ¼ inch air space above ZP layer | Particle size: <250μ<br>Adsorption: 47 mg $NH_4^+$—N per gm<br>Prep: isopropanol additive; sequential addition and hydrothermal treatment<br>(Sol Gel ZP # 58, 45) | 45 min | 6 gm | 90% | — | 6.5 psi max |
| 9 | 2 rings | Particle size: <250μ<br>Adsorption: 45 mg $NH_4^+$—N per gm<br>Prep: isopropanol additive; sequential addition and hydrothermal treatment<br>(Sol Gel ZP # 59, 47, 45) | 150 min | 18.8 gm | 35% | 29 gm | 9 psi max |
| 10 | Thick cellulose sponge; 2 rings | Particle size: <250μ<br>Adsorption: 40 mg $NH_4^+$—N per gm<br>Prep: isopropanol additive; sequential addition and NO hydrothermal treatment<br>(Sol Gel ZP # 41, 40) | 150 min | 20.7 gm | 20% | 26 gm | 16 psi max |
| 11 | Thick cellulose sponge; 1 ring | Particle size: <90μ<br>Adsorption: 47 mg $NH_4^+$—N per gm<br>Prep: acetic acid additive; sequential addition and hydrothermal treatment<br>(Sol Gel ZP # 17, 16) | 135 min | 16.7 gm | 30% | 24 gm | 16.5 psi max |
| 12 | Thick cellulose sponge; blended with glass beads | Particle size; <90μ<br>Adsorption: 42 mg $NH_4^+$—N per gm<br>Prep; isopropanol additive; simultaneous addition and NO hydrothermal treatment<br>(Sol Gel ZP # 1) | 195 min | 20 gm | 20% | 25 gm | 13 psi max |
| 13 | Thick cellulose sponge; blended with glass beads | Particle size: <90μ<br>Adsorption: 45 mg $NH_4^+$—N per gm<br>Prep: acetic acid additive; simultaneous addition and hydrothermal treatment<br>(Sol Gel ZP # 4, 5) | 150 min | 19.8 gm | 20% | 25 gm | 15.5 psi max |
| 14 | 1 thin cellulose sponge; blended with glass beads | Particle size: <90μ<br>Adsorption: 45 mg $NH_4^+$—N per gm<br>Prep: isopropanol additive; simultaneous addition and NO hydrothermal treatment<br>(Sol Gel ZP # 6) | 135 min | 19.4 gm | 30% | 28 gm | 29 psi max |
| 15 | 2 thin cellulose sponges | Particle size: <180μ<br>Adsorption: 49 mg $NH_4^+$—N per gm<br>Prep: Max amount of $H_{3PO4}$<br>(Sol Gel ZP # 13, 29) | 135 min | 16 gm | 25% | 21 gm | 11 psi max |
| 16 | 2 thin cellulose sponges | Particle size: <180μ<br>Adsorption: 43 mg $NH_4^+$—N per gm<br>Prep: Soda ash additive<br>(Sol Gel ZP # 54, 55) | 140 min | 18 gm | 25% | 24 gm | 9.5 psi max |

The BET surface area, pore volume, monolayer volume, and pore size distribution of six sol gel ZP samples were analyzed by using different additives and processing conditions, in comparison with the BZS ZP product as a control. BET surface area can be measured by known standards, such as ASTM D 6556. Nitrogen is the typically used adsorptive for surface area determinations. All BET values indicated herein are inclusive of at least BET nitrogen surface area. Other gases may be used, such as krypton or argon. The pore volume, (Langmuir) monolayer volume, and pore size distribution can be determined by an adsorption method or mercury porosimetry. All pore volume, monolayer volume, and pore size distribution values indicated herein are inclusive of values determined using mercury porosimetry. As indicated, the pore volumes and pore sizes also can be determined with adsorption methods known in the industry. The BET surface area, pore volume, monolayer volume, and pore size distribution can be measured, for example, using a commercial porosimetry designed to make these various analyses, such as Micromeritics Autopore series porosimeters, or by other porosimetry instruments and/or techniques that are applicable to ZrP.

The results for BET surface area, pore volume, monolayer volume, and pore size determinations for various sol gel ZP samples representing embodiments of the present invention and comparison and control sol gels are indicated in Table 6.

TABLE 6

| Sample No. | Preparation Method | Particle Size (microns) | BET Surface Area $m^2/gm$ | Pore volume Ml/gm | Monolayer volume Ml/gm (STP) | Pore size Nm |
|---|---|---|---|---|---|---|
| 8 | Using alcohol additive without hydrothermal treatment | <90 (incl. fines) | 14.17 | 0.0363 | 3.2557 | 20-80 (45.92%) |
| 7 | Using acetic acid additive without hydrothermal treatment (with HCl) | 45-90 | 27.136 | 0.0802 | 6.2347 | 20-80 (48.85%) |
| 56 | Using soda ash additive without hydrothermal treatment | 45-180 | 2.458 | 0.007 | 0.5649 | 20-80 (35.79%) |
| 13 | Using acetic acid additive without hydrothermal treatment (without HCl) | 45-90 | 2.245 | 0.008 | 0.5158 | 20-80 (40.57%) |
| 54 | Using soda ash additive with hydrothermal treatment | 45-180 | 1.499 | 0.0063 | 0.3445 | 20-80 (34.91%) |
| 29 | Using high phosphoric acid and acetic acid additive | 45-90 | 2.425 | 0.0076 | 0.5571 | 20-80 (33.62%) |
| ZP Ctrl-BZS ZP Control Sample | | | 1.622 | 0.0065 | 0.3726 | 20-80 (39.89%) |

The effect of swelling of sol gel ZP on cartridge design was investigated by measuring the difference in particle density of the material in dialysate and cyclohexane for various sol gel ZP samples representing embodiments of the present invention and comparison or control sol gel ZP samples.

Figure 2:
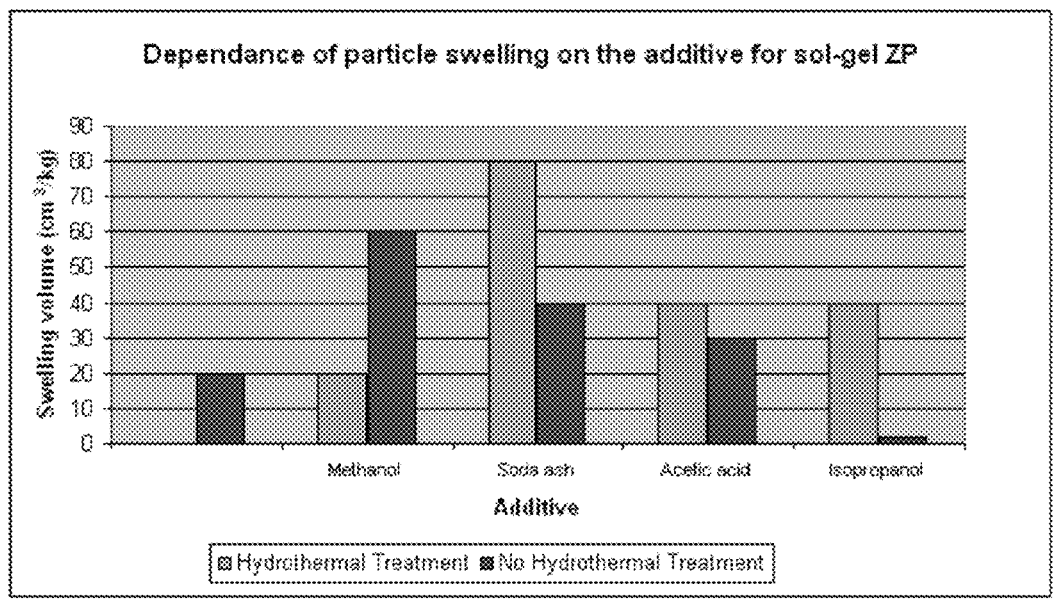
FIG. 2 is a graph showing the dependence of particle swelling, as swelling volume ($cm^3$/kg), on an additive that is combined with zirconium oxychloride before precipitation with phosphoric acid for sol-gel production.

The results for the swelling tests are indicated in Table 7 and shown in FIG. 2.

TABLE 7

| | | Swelling Volume | |
|---|---|---|---|
| Sample # | Additive | ($cm^3/50$ g) | ($cm^3/kg$) |
| Hydrothermal treatment | | | |
| 9 | Methanol | 1 | 20 |
| 57 | Soda ash | 4 | 80 |

TABLE 7-continued

| | | Swelling Volume | |
|---|---|---|---|
| Sample # | Additive | ($cm^3/50$ g) | ($cm^3/kg$) |
| 18 | Acetic acid | 2 | 40 |
| 26 | Isopropanol | 2 | 40 |
| No Hydrothermal Treatment | | | |
| 67 | Control | 1 | 20 |
| 8 | Methanol | 3 | 60 |
| 56 | Soda ash | 2 | 40 |
| 14 | Acetic Acid | 1.5 | 30 |
| 21 | Isopropanol | 0.1 | 2 |

Results and Discussions:

With respect to result for $NH_4^-N$ adsorption quality of product, the sol gel ZP has about 100% improvement over the BZS ZP product, which has $NH_4^+$—N adsorption capacity of about 20 mg/g ZP. As shown in Table 4, the $NH_4^+$—N adsorption capacity of sol gel ZP may vary with the process conditions. These conditions are further discussed below in order to, for example, guide maximization of $NH_4^+$—N adsorption quality of product, prevent excessive agglomeration upon drying, and formation of fine particles.

With respect to mixing weight ratio of ZOC to $H_3PO_4$, the results indicate that the increase of the mixing weight ratio of ZOC to 76% $H_3PO_4$ from 500 g:600 g to 500 g:800 g can increase the $NH_4^+$—N adsorption capacity from about 45 mg/gm ZP to 49 mg/gm ZP. However, no more improvement appears to be attainable upon increasing the amount of 76% $H_3PO_4$ further, even up to 500 g:1400 g, although the product is more crystalline when the amount and concentration of $H_3PO_4$ increase. Furthermore, cartridge performance test results indicate no difference in the $NH_4^+$—N adsorption capacity by the cartridge as caused by such improvement of the material because, apparently, it is affected more by the flow dynamics due to bed porosity and particle size of the material. Thus, the weight mixing ratio of ZOC to 76% $H_3PO_4$ at 500 g:600 g can be considered to be optimum for the sol gel process in view of this stage of experiments.

With respect to simultaneous addition of ZOC and $H_3PO_4$, simultaneous addition of ZOC and $H_3PO_4$ helps to produce sol gel ZP particles with more uniform composition and particle size during the precipitation reaction, thus reducing agglomeration of the product upon drying and formation of fine particles. Simultaneously, the $NH_4^+$—N adsorption capacity of the product can be improved consistently to the range of 40 mg/g ZP-45 mg/g ZP even without the need of hydrothermal treatment.

With respect to hydrothermal treatment, hydrothermal treatment of the crude sol gel ZP in the presence of dilute $H_3PO_4$ is found to improve the $NH_4^+$—N capacity of the product consistently to the range 40 mg/g ZP-45 mg/g ZP. It has the advantage of improving the crystal structure and poor adsorption quality of product caused by improper precipitation process (e.g. sequential addition instead of simultaneous addition of ZOC and $H_3PO_4$). The method is simply heating the crude sol gel ZP slurry in DI or RO water to about 90° C. and maintaining the temperature for about 1 hour, with the concentration at about 500 gm per 2 L and 150 gm 76% $H_3PO_4$ added to the slurry before the heating.

With respect to the type of additive to ZOC and its amount, the following types and amounts of additives to the ZOC solution shown in the Table below are found to be effective to prevent gelation of the product during the precipitation process and improve the $NH_4^+$—N adsorption of it by enhancing its porosity.

TABLE 8

| Type of additive | Amount based on 500 gm ZOC | $NH_4^+$—N adsorption capacity of product |
| --- | --- | --- |
| Alcohol (isopropanol or 95% methanol) | 300 ml | 40-45 mg $NH_4^+$—N/gm ZP |
| Acetic acid | 200 ml | 40-45 mg $NH_4^+$—N/gm ZP |
| Soda ash | 40 gm | 40-42 mg $NH_4^+$—N/gm ZP |

As indicated, the BET surface area, pore volume and pore size distribution of six sol gel ZP samples were analyzed by using different additives and processing conditions, in comparison with the BZS ZP product as control are shown in Table 6. Although there is no direct relationship between the gas adsorption and the ion-exchange reaction with $NH_4^+$—N, the data in general indicates that sol gel ZP is more porous than the BZS ZP.

With respect to the amount of concentrated HCl added to ZOC, the particle size of sol gel ZP can optionally be improved by adding a small amount of concentrated HCl to the ZOC solution (about 40 ml per 650 ml ZOC solution). The particle size of precipitate can then be controlled to a desirable range in combination with the agitation rate and optional concentration of $H_3PO_4$.

With respect preliminary cartridge performance, as shown in Table 5, preliminary cartridge performance of using sol gel ZP prepared according to various conditions can be summarized as follows. With regard to the effect of swelling of sol gel ZP on cartridge design, the high porosity of sol gel ZP can cause an initial swelling of the ZP bed in the cartridge by the absorption of the dialysate saturated with $CO_2$ gas, followed by the shrinkage of the bed as the $CO_2$ gas level in dialysate is reduced. The swelling data of some typical sol gel ZP samples prepared by different additives and processing conditions in comparison with that of BZS ZP are shown in Table 7 and FIG. 2. As indicated, the data is taken by measuring the difference in particle density of the material in dialysate and cyclohexane. It can be seen that sol gel ZP in general has more swelling than BZS ZP.

With respect to the effect of particle size on $NH_4^+$—N leakage and flow resistance pressure, sol gel ZP with particle size sieved between 45 microns and 90 microns does not cause any flow resistance (with back pressure less than 12 psi) when a sponge is put above the ZP layer. Furthermore, sol gel ZP sieved below 180 microns has no $NH_4^+$—N leakage even though the bed is loosely packed. This indicates the sol gel ZP can adsorb $NH_4^+$—N rapidly due to the high porosity or sponge nature of the material.

With respect to correlation of cartridge urea-N capacity to $NH_4^+$—N capacity data of material, a consistent 17 gm-20 gm UNC is obtainable with no $NH_4^+$—N leakage when 800 gm sol gel ZP is used in the REDY cartridge despite less than optimal flow causing about 30% unused ZP for $NH_4^+$—N adsorption. The UNC is expected to be increased when the material is used in a bigger canister causing a slower flow velocity and hence a more uniform flow.

With respect to process performance, when a sufficient amount of alcohol, acetic acid or soda ash is added to the ZOC solution, there is no gelation problem in the sol gel ZP precipitation process. The product material can be filtered easily during the washing process and no agglomeration occurs upon drying.

With respect to process efficiency, sol gel ZP precipitation process at ambient temperature can be easily performed and can greatly increase the efficiency of making ZP especially when no hydrothermal treatment is involved. The simultaneous addition of ZOC and $H_3PO_4$ can improve the adsorption quality of the product to the extent such that the hydrothermal treatment can be skipped.

With respect to particle size control and amount of fine particles, particle size control of the product can be facilitated by making the sol gel ZP particle size a little bigger during the precipitation process (90-180) microns followed by grinding the dried product powder to the desirable range with a particle size control grinder. The amount of fine particles (below 45 microns) in a lab scale batch can be less than 5%.

The sol gel process of the present invention is the highly efficient and economical method of manufacturing ZP when the gelation problem has been solved by using additives to the ZOC solution according to the present invention. These results indicate an enhanced design of the sol gel process can be expected to produce ZP product with $NH_4^+$—N adsorption capacity of (40-45) mg/g, which is about 80% higher than that of the current product.

In these studies, a cartridge using 800 gm sol gel ZP removes only 17 to 20 gm $NH_4^+$—N from dialysate with about 30-35% unused ZP, which is thought to predict that a urea-N capacity of 30 gm can be attainable when the material is fully utilized in $NH_4^+$—N adsorption, such as for sorbent dialysis.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of making zirconium phosphate particles comprising:
   (a) combining zirconium oxychloride with at least one oxygen containing, monofunctional, organic additive having a molecular weight of 20-80 and in an amount of from 25 wt % to 70 wt % based on the weight of the zirconium oxychloride in an aqueous solvent to form a solution, and
   (b) combining the solution obtained in (a) with phosphoric acid and removing the at least one oxygen containing, monofunctional, organic additive to obtain zirconium phosphate particles by sol gel precipitation.

2. The method of claim 1, wherein the phosphoric acid in step (b) has a temperature of from about 90° C. to about 100° C.

3. The method of claim 1, wherein the oxygen containing, monofunctional, organic additive forms a complex with zirconium ions in the solution.

4. The method of claim 1, wherein zirconium oxychloride is dissolved in the aqueous solvent and then the oxygen containing, monofunctional, organic additive is added to form the solution of step (a).

5. The method of claim 1, wherein the zirconium oxychloride is present in the aqueous solvent at a concentration of from about 1.1 to about 1.5 g/ml.

6. The method of claim 1, wherein the zirconium oxychloride is present in the aqueous solvent up to a saturation concentration.

7. The method of claim 1, wherein the oxygen containing, monofunctional, organic additive is present in the aqueous solvent and then the zirconium oxychloride is added to form the solution of step (a).

8. The method of claim 3, wherein the oxygen containing, monofunctional, organic additive is present in the solution of step (a) in a molar amount sufficient so that substantially all of the zirconium ions in the solution are converted to the complex.

9. The method of claim 1, wherein the oxygen containing, monofunctional, organic additive forms a soluble polymer complex with zirconium ions.

10. The method of claim 1, wherein the oxygen containing, monofunctional, organic additive is an alcohol, a carboxylate, or combinations thereof.

11. The method of claim 1, wherein the oxygen containing, monofunctional, organic additive is methanol, ethanol, propanol, isopropanol, acetic acid, propionic acid, or combinations thereof.

12. The method of claim 1, wherein the phosphoric acid comprises orthophosphoric acid.

13. The method of claim 1, further comprising:
   (c) subjecting an aqueous slurry containing zirconium phosphate particles obtained from step (b) to a heat treatment carried out at a temperature of from about 90° C. to about 100° C.

14. The method of claim 13, wherein the heat treatment of step (c) is carried out for at least one hour.

15. The method of claim 13, wherein the aqueous slurry of step (c) is agitated during the heat treatment.

16. The method of claim 1, wherein in step (b), the solution obtained in step (a) and a solution of phosphoric acid are combined so that zirconium ions and phosphate groups are present in a molar ratio of about 1 to about 3 of zirconium to phosphate.

17. The method of claim 1, wherein the phosphoric acid has a molarity of from about 1.5 moles/L to about 3 moles/L.

18. The method of claim 1, further comprising combining the solution obtained in (a) with HCl before step (b).

19. The method of claim 1, further comprising isolating and drying the zirconium phosphate particles obtained in step (b) to obtain a free flowing powder.

20. A method of making zirconium phosphate particles having a controlled particle size comprising forming zirconium phosphate particles by sol gel precipitation by the method of claim 1, wherein the zirconium phosphate particles have a particle size and particle size distribution obtained by controlling one or more of the following parameters: (a) the rate at which the solution of zirconium oxychloride and oxygen containing, monofunctional, organic additive is added to the reaction vessel, (b) the rate at which the solution of phosphoric acid is added to the reaction vessel, (c) the pH of the solution of phosphoric acid, (d) the concentration of zirconium oxychloride, oxygen containing, monofunctional, organic additive, or phosphoric acid in the reaction vessel, (e) the presence of HCl in the reaction vessel, (f) the speed of the agitator, or (g) any combination thereof.

* * * * *